(12) United States Patent
Tyurin et al.

(10) Patent No.: US 11,512,336 B1
(45) Date of Patent: Nov. 29, 2022

(54) METHOD FOR METHANOL FREE CULTURING OF METHYLOTROPHIC YEAST FOR THE BIOSYNTHESIS OF ADDED VALUE PRODUCTS

(71) Applicant: BioBoost Synbio Consulting Inc., Burnaby (CA)

(72) Inventors: Oleg Tyurin, Burnaby (CA); Mingyang Sun, Burnaby (CA)

(73) Assignee: BioBoost Synbio Consulting Inc., Burnaby (CA)

( * ) Notice: Subject to any disclaimer, the term of this patent is extended or adjusted under 35 U.S.C. 154(b) by 0 days.

(21) Appl. No.: 17/478,241

(22) Filed: Sep. 17, 2021

Related U.S. Application Data

(60) Provisional application No. 63/214,376, filed on Jun. 24, 2021.

(51) Int. Cl.
*C12P 21/02* (2006.01)
*C12N 1/16* (2006.01)
*C12N 9/02* (2006.01)
*C12N 15/81* (2006.01)
*C12N 1/32* (2006.01)

(52) U.S. Cl.
CPC ............... *C12P 21/02* (2013.01); *C12N 1/16* (2013.01); *C12N 1/32* (2013.01); *C12N 9/0089* (2013.01); *C12N 15/815* (2013.01)

(58) Field of Classification Search
CPC .. C12P 21/02; C12N 1/16; C12N 1/32; C12N 9/0089; C12N 15/815
See application file for complete search history.

(56) References Cited

U.S. PATENT DOCUMENTS

2003/0215920 A1* 11/2003 Cregg .................. C12N 9/0008
435/69.1
2008/0153126 A1* 6/2008 Hartner ................ C12N 15/815
435/34

OTHER PUBLICATIONS

Inan M et al. Non-repressing Carbon Sources for Alcohol Oxidase (AOX1) Promoter of Pichia pastoris. 2001. Journal of Bioscience and Bioengineering. vol. 92, No. 6, 585-589. (Year: 2001).*
Kizer L et al. Application of Functional Genomics to Pathway Optimization for Increased Isoprenoid Production. 2008. Applied and Environmental Microbiology, p. 3229-3241. (Year: 2008).*
Krainer FW et al. Recombinant protein expression in Pichia pastoris strains with an engineered methanol utilization pathway. 2012. Microbial Cell Factories. 11:22 (Year: 2012).*
Prather KLJ et al. De novo biosynthetic pathways: rational design of microbial chemical factories. 2008. Current Opinion in Biotechnology. 19:468-474. (Year: 2008).*
Young CL et al. Recombinant Protein Expression and Purification: a comprehensive review of affinity tags and microbial applications. 2012. Biotechnology Journal. 7, 620-634. (Year: 2012).*
Sodium Formate. Sigma-Aldrich. 2016. p. 1. (Year: 2016).*
ISSN 0026-2617, Microbiology 2015, "Deletion of the FLD Gene in Methylotrophic Yeasts Komagataella phaffii and Komagataella kurtzmanii Results in Enhanced Induction of the AOX1 Promoter in Response to Either Methanol or Formate" Tyurnin and Kozlov, vol. 84, No. 3, pp. 408-411.

* cited by examiner

*Primary Examiner* — Paul J Holland
(74) *Attorney, Agent, or Firm* — Michael R Williams; Ryan W Dupuis; Ade & Company Inc.

(57) ABSTRACT

Described herein is a method for producing a transgenic cell product wherein the gene of interest is operably linked to an inducible promoter other than AOX1. Production of the transgenic cell product is activated when the host cell is grown on a non-repressing carbon source for de-repressing the inducible promoter and an amount of an inducer compound selected from the group consisting of: formaldehyde; S-formylglutathione; S-hydroxymethyl glutathione; formic acid; an alkali metal salt of formic acid; and an alkaline earth metal salt of formic acid; sufficient to induce the inducible promoter is added to the host cell culture.

22 Claims, 4 Drawing Sheets

Specification includes a Sequence Listing.

SEQUENCE LISTING

<160> NUMBER OF SEQ ID NOS: 21

<210> SEQ ID NO 1
<211> LENGTH: 1032
<212> TYPE: DNA
<213> ORGANISM: Pichia pastoris

<400> SEQUENCE: 1

```
attctggccc ttgcacctga tcgcgaaggt ggaaatggca gaaggatcag cctggacgaa    60
gcaaccagtt ccaactgcta agtaaagaag atgctagacg aaggagactt cagaggtgaa   120
aagtttgcaa gaagagagct gcgggaaata aattttcaat ttaaggactt gagtgcgtcc   180
atattcgtgt acgtgtccaa ctgttttcca ttacctaaga aaacataaa gattaaaaag    240
ataaacccaa tcgggaaact ttagcgtgcc gtttcggatt ccgaaaaact tttggagcgc   300
cagatgacta tggaaagagg agtgtaccaa aatggcaagt cggggctac tcaccggata    360
gccaatacat tctctaggaa ccagggatga atccaggttt tgttgtcac ggtaggtcaa    420
gcattcactt cttaggaata tctcgttgaa agctacttga atcccattg ggtgcggaac    480
cagcttctaa ttaaatagtt cgatgatgtt ctctaagtgg gactctacgg ctcaaacttc   540
tacacagcat catcttagta gtcccttccc aaaacaccat tctaggtttc ggaacgtaac   600
gaaacaatgt tcctctcttc acattgggcc gttactctag ccttccgaag aaccaataaa   660
agggaccggc tgaaacgggt gtggaaactc tgtccagtt tatggcaaag gctacagaaa    720
tcccaatctt gtcgggatgt tgctcctccc aaacgccata ttgtactgca gttggtgcgc   780
attttaggga aaatttaccc cagatgtcct gattttcgag ggctacccccaactccctgt   840
gcttatactt agtctaattc tattcagtgt gctgacctac acgtaatgat gtcgtaaccc   900
agttaaatgg ccgaaaaact atttaagtaa gtttatttct cctccagatg agactctcct   960
tcttttctcc gctagttatc aaactataaa cctatttac ctcaaatacc tccaacatca   1020
cccacttaaa ca                                                       1032
```

<210> SEQ ID NO 2
<211> LENGTH: 1542
<212> TYPE: DNA
<213> ORGANISM: Pichia pastoris

<400> SEQUENCE: 2

```
ttatttttg accgaattct ttttttcaga ccatatgacc ggtccatctt ctacgggggg      60
attatctatg ctttgacctc tatcttgatt ctttttatgat tcaaatcact tttacgttat   120
ttattactta ctggttattt acttagcgcc ttttctgaaa acatttact aaaaatcata    180
catcggcact ctcaaacacg acagattgtg atcaagaagc agagacaatc accactaagg   240
ttgcacattt gagccagtag gctcctaata gaggttcgat acttatttg ataatacgac   300
atattgtctt acctctgaat gtgtcaatac tctctcgttc ttcgtctcgt cagctaaaaa    360
tataacactt cgagtaagat acgcccaatt gaaggctacg agataccaga ctatcactag   420
```

```
tagaactttg acatctgcta aagcagatca aatatccatt tatccagaat caattacctt    480
cctttagctt gtcgaaggca tgaaaaagct acatgaaaat ccccatcctt gaagttttgt    540
cagcttaaag gactccattt cctaaaattt caagcagtcc tctcaactaa attttttcc     600 attcctctgc acccagccct cttcatcaac cgtccagcct tctcaaaagt ccaatgtaag    660
tagcctgcaa attcaggtta caacccctca atttccatc caagggcgat ccttacaaag    720
ttaatatcga acagcagaga ctaagcgagt catcatcacc acccaacgat ggtgaaaaac    780
tttaagcata gattgatgga gggtgtatgg cacttggcgg ctgcattaga gtttgaaact    840
atggggtaat acatcacatc cggaactgat ccgactccga gatcatatgc aaagcacgtg    900
atgtaccccg taaactgctc ggattatcgt tgcaattcat cgtcttaaac agtacaagaa    960
actttattca tgggtcattg gactctgatg aggggcacat ttccccaatg attttttggg   1020
aaagaaagcc gtaagaggac agttaagcga aagagacaag acaacgaaca gcaaaagtga   1080
cagctgtcag ctaccagtg gacagttggg agtttccaat tggttggttt tgaatttta     1140 cccatgttga gttgtccttg cttctccttg caaacaatgc aagttgataa gacatcacct   1200
tccaagatag gctattttg tcgcataaat ttttgtctcg gagtgaaaac cccttttatg    1260
tgaacagatt acagaagcgt cctacccttc accggttgag atggggagaa aattaagcga   1320
tgaggagacg attattggta taaaagaagc aaccaaaatc ccttattgtc cttttctgat   1380
cagcatcaaa gaatattgtc ttaaaacggg cttttaacta cattgttctt acacattgca   1440
aacctcttcc ttctatttcg gatcaactgt attgactaca ttgatctttt taacgaagt    1500 ttacgactta ctaaatcccc acaaacaaat caactgagaa aa                      1542

<210> SEQ ID NO 3
<211> LENGTH: 1032
<212> TYPE: DNA
<213> ORGANISM: Pichia pastoris

<400> SEQUENCE: 3
attctggccc ttgcacctga tcgcgaaggt ggaaatggca gaaggatcag cctggacgaa     60
gcaaccagtt ccaactgcta agtaaagaag atgctagacg aaggagactt cagaggtgaa    120
aagtttgcaa gaagagagct gcgggaaata aattttcaat ttaaggactt gagtgcgtcc    180
atattcgtgt acgtgtccaa ctgttttcca ttacctaaga aaaacataaa gattaaaaag    240
ataaacccaa tcgggaaact ttagcgtgcc gtttcggatt ccgaaaaact tttggagcgc    300
cagatgacta tggaaagagg agtgtaccaa aatggcaagt cggggggctac tcaccggata    360 gccaatacat tctctaggaa ccagggatga atccaggttt tgttgtcac ggtaggtcaa     420 gcattcactt cttaggaata tctcgttgaa agctacttga atcccattg ggtgcggaac     480 cagcttctaa ttaaatagtt cgatgatgtt ctctaagtgg gactctacgg ctcaaacttc    540
tacacagcat catcttagta gtcccttccc aaaacaccat tctaggtttc ggaacgtaac    600
gaaacaatgt tcctctcttc acattgggcc gttactctag ccttccgaag aaccaataaa    660
agggaccggc tgaaacgggt gtggaaactc ctgtccagtt tatggcaaag ctacagaaaa    720
tcccaatctt gtcgggatgt tgctcctccc aaacgccata ttgtactgca gttggtgcgc    780
attttaggga aaatttaccc cagatgtcct gattttcgag ggctaccccc aactccctgt    840
gcttatactt agtctaattc tattcagtgt gctgacctac acgtaatgat gtcgtaaccc    900
agttaaatgg ccgaaaaact atttaagtaa gtttatttct cctccagatg agactctcct   960 tctttttctcc gctagttatc aaactataaa cctattttac ctcaaatacc tccaacatca  1020
```

-continued

```
cccacttaaa ca                                                     1032

<210> SEQ ID NO 4
<211> LENGTH: 560
<212> TYPE: DNA
<213> ORGANISM: Pichia pastoris

<400> SEQUENCE: 4
atcttcattg atgaaacgtt gtgatcggtg tgacttttat agtaaaagct acaactgttt    60
gaaataccaa gatatcattg tgaatggctc aaaagggtaa tacatctgaa aaacctgaag   120
tgtggaaaat tccgatggag ccaactcatg ataacgcaga agtcccattt tgccatcttc   180
tcttggtatg aaacggtaga aaatgatccg agtatgccaa ttgatactct tgattcatgc   240
cctatagttt gcgtagggtt taattgatct cctggtctat cgatctggga cgcaatgtag   300
accccattag tggaaacact gaaagggatc caacactcta ggcggacccg ctcacagtca   360
tttcaggaca atcaccacag gaatcaacta cttctcccag tcttccttgc gtgaagcttc   420
aagcctacaa cataacactt cttacttaat ctttgattct cgaattgttt acccaatctt   480
gacaacttag cctaagcaat actctggggt tatatatagc aattgctctt cctcgctgta   540
gcgttcattc catctttcta                                               560

<210> SEQ ID NO 5
<211> LENGTH: 609
<212> TYPE: DNA
<213> ORGANISM: Pichia pastoris

<400> SEQUENCE: 5
tgtcatctgc tgatgctgtg agggagaaag aagtaggggt gatacatggt ttataggcaa    60
agcatgtttg tttcagatca aagattagcg tttcaaagtt gtggaaaagt gaccatgcaa   120
caatatgcaa cacattcgga ttatctgata agtttcaaag ctactaagta agcccgtttc   180
aagtctccag accgacatct gccatccagt gattttctta gtcctgaaaa atacgatgtg   240
taaacataaa ccacaaagat cggcctccga ggttgaaccc ttacgaaaga gacatctggt   300
agcgccaatg ccaaaaaaaa atcacaccag aaggacaatt cccttccccc ccagcccatt   360
aaagcttacc atttcctatt ccaatacgtt ccatagaggg catcgctcgg ctcattttcg   420
cgtgggtcat actagagcgg ctagctagtc ggctgtttga gctctctaat cgaggggtaa   480
ggatgtctaa tatgtcataa tggctcacta tataaagaac ccgcttgctc aaccttcgac   540 tccttttcccg atcctttgct tgttgcttct tctttttataa caggaaacaa aggaatttat   600
acactttaa                                                          609

<210> SEQ ID NO 6
<211> LENGTH: 704
<212> TYPE: DNA
<213> ORGANISM: Pichia pastoris

<400> SEQUENCE: 6
aaattaatcc ataagataag gcaaatgtgc ttaagtaatt gaaaacagtg ttgtgattat    60
ataagcatgg tatttgaata gaactactgg ggttaactta tctagtagga tggaagttga   120
gggagatcaa gatgcttaaa gaaaaggatt ggccaatatg aaagccataa ttagcaatac   180
ttatttaatc agataattgt ggggcattgt gacttgactt ttaccaggac ttcaaacctc   240
aaccatttaa acagttatag aagacgtacc gtcactttg cttttaatgt gatctaaatg   300
```

```
tgatcacatg aactcaaact aaaatgatat ctttttactgg acaaaaatgt tatcctgcaa    360
acagaaagct ttcttctatt ctaagaagaa catttacatt ggtgggaaac ctgaaaacag    420
aaaataaata ctccccagtg accctatgag caggattttt gcatccctat tgtaggcctt    480
tcaaactcac acctaatatt tcccgccact cacactatca atgatcactt cccagttctc    540
ttcttcccct attcgtacca tgcaacccct acacgccttt tccatttcgg ttcggatgcg    600
acttccagtc tgtggggtac gtagcctatt ctcttagccg gtatttaaac atacaaattc    660
acccaaattc taccttgata aggtaattga ttaatttcat aaat                     704

<210> SEQ ID NO 7
<211> LENGTH: 501
<212> TYPE: DNA
<213> ORGANISM: Pichia pastoris

<400> SEQUENCE: 7
tccaaaccaa acggtctagc aaaaacgata actttaaaga acttttcaat tggttttgta     60
cactaccacc ggtttactac ctctgccttc ggttcttctc ctcacatttt tcgcaactgg    120
gatagcgtag cctaaagtgt cacatgctcg ctgctcacat tccctacaca acagagattg    180
tcagcagagg aaattgagct ccaccattca acacttgtgg atttatgata gtctgtgcta    240
tcagctctct tttttttgtt gctgtagaat ttaccgtgct agcaaccttt taaactttgt    300
ttagctctcc ttccctcttc cattcatctg tttcggtccg atccgtctct ggtcatctcc    360
tccgcatttt tttttaccg ttagcgatag gggtcagatc aattcaatca gttttggcaa    420
gggtatttaa aggtggcgaa atccccctcc gtttgttgaa cacatccaac tattctcaac    480
ccaaccatct aactaatcgt a                                               501

<210> SEQ ID NO 8
<211> LENGTH: 1212
<212> TYPE: DNA
<213> ORGANISM: Pichia pastoris

<400> SEQUENCE: 8
cgcagcgttt tctgacggta ctagaggact cttaggggaa ggtagaatca ataaagatca     60
tattaggtaa gcaaattttg gatggaatag gagactaggt gtggatgcgc gatctcgcca    120
aattgcacga ccagagtgga tgccggatgg tggtaaaccg tttcttcctt tttaccaccc    180
aagtgcgagt gaaacacccc atggctgctc tccgattgcc cctctacagg cataagggtg    240
tgactttgtg ggcttgaatt ttacaccccc tccaacttttt ctcgcatcaa ttgatcctgt    300
taccaatatt gcatgcccgg aggagacttg cccctaatt tcgcggcgtc gtcccggatc    360
gcagggtgag actgtagaga ccccacatag tgacaatgat tatgtaagaa gagggggtg     420 attcggccgg ctatcgaact ctaacaacta gggggtgaa caatgcccag cagtcctccc    480
cactctttga caaatcagta tcaccgatta acaccccaaa tcttattctc aacggtccct    540
catccttgca cccctctttg gacaaatggc agttagcatt ggtgcactga ctgactgccc    600
aaccttaaac ccaaatttct tagaaggggc ccatctagtt agcgaggggt gaaaaattcc    660
tccatcggag atgtattgac cgtaagttgc tgcttaaaaa aaatcagttc agatagcgag    720 actttttttga tttcgcaacg ggagtgcctg ttccattcga ttgcaattct caccccttct    780
gcccagtcct gccaattgcc catgaatctg ctaatttcgt tgattcccac cccccttttcc   840 aactccacaa attgtccaat ctcgtttttcc atttgggaga atctgcatgt cgactacata    900
aagcgaccgg tgtccgaaaa gatctgtgta gttttcaaca ttttgtgctc ccccgctgt     960
```

```
ttgaaaacgg gggtgagcgc tctccggggt gcgaattcgt gcccaattcc tttcaccctg    1020
cctattgtag acgtcaaccc gcatctggtg cgaatatagc gcaccccaa tgatcacacc    1080 aacaattggt ccacccctcc ccaatctcta atattcacaa ttcacctcac tataaatacc    1140
cctgtcctgc tcccaaattc ttttttcctt cttccatcag ctactagctt ttatcttatt    1200
tactttacga aa                                                        1212
```

<210> SEQ ID NO 9
<211> LENGTH: 258
<212> TYPE: DNA
<213> ORGANISM: Pichia pastoris

<400> SEQUENCE: 9

```
tgtgtctgta aatttaaatc caagaaaaa taaagggcac tacatagaac aacacaatca     60
acctacatag ctctcttttt tttttttttt ttttttttct tttttgtttt ttctcaattt    120
tcttcatttt ttgcattgtt actactctcc cattaaggga aattctacca ggaaaaccga    180
agaagacaaa tgcaaaaggg aaatatgaat acgcatgtat gcgcgcaaaa ccgcacttac    240
agagggcatt aggacatt                                                  258
```

<210> SEQ ID NO 10
<211> LENGTH: 552
<212> TYPE: DNA
<213> ORGANISM: Pichia pastoris

<400> SEQUENCE: 10

```
agcaatgata taaacaacaa ttgagtgaca ggtctacttt gttctcaaaa ggccataacc     60
atctgtttgc atctcttatc accacaccat cctcctcatc tggccttcaa ttgtggggaa    120
caactagcat cccaacacca gactaactcc acccagatga aaccagttgt cgcttaccag    180
tcaatgaatg ttgagctaac gttccttgaa actcgaatga tcccagcctt gctgcgtatc    240
atccctccgc tattccgccg cttgctccaa ccatgtttcc gccttttcg aacaagttca    300 aataccctatc tttggcagga cttttcctcc tgcctttttt agcctcaggt ctcggttagc    360
ctctaggcaa attctggtct tcatacctat atcaactttt catcagatag cctttgggtt    420
caaaaaagaa ctaaagcagg atgcctgata tataaatccc agatgatctg cttttgaaac    480
tattttcagt atcttgattc gtttacttac aaacaactat tgttgatttt atctggagaa    540
taatcgaaca aa                                                        552
```

<210> SEQ ID NO 11
<211> LENGTH: 1102
<212> TYPE: DNA
<213> ORGANISM: Pichia pastoris

<400> SEQUENCE: 11

```
cataatgata tttgagggtg ttagttactt cgtctccaga gtagcttata gggagaaaaa     60
ccgagacaac gatggaactc ccatgtagat tccaccgccc caattactgt tttgggcaat    120
cctgttgata agacgcattc tagagttgtt tcatgaaagg gttacgggtg ttgattggtt    180
tgagatatgc cagaggacag atcaatctgt ggtttgctaa actggaagtc tggtaaggac    240
tctagcaagt ccgttactca aaagtcata ccaagtaaga ttacgtaaca cctgggcatg    300
actttctaag ttagcaagtc accaagaggg tcctatttaa cgtttggcgg tatctgaaac    360
acaagacttg cctatcccat agtacatcat attacctgtc aagctatgct acccacaga    420
```

```
aatacccca  aagttgaagt  gaaaaaatga  aaattactgg  taacttcacc  ccataacaaa       480
cttaataatt  tctgtagcca  atgaaagtaa  accccattca  atgttccgag  atttagtata       540 cttgcccta   taagaaacga  aggatttcag  cttccttacc  ccatgaacag  aaatcttcca       600
tttacccccc  actggagaga  tccgcccaaa  cgaacagata  atagaaaaaa  gaaattcgga       660
caaatagaac  actttctcag  ccaattaaag  tcattccatg  cactcccttt  agctgccgtt       720
ccatcccttt  gttgagcaac  accatcgtta  gccagtacga  aagaggaaac  ttaaccgata       780
ccttggagaa  atctaaggcg  cgaatgagtt  tagcctagat  atccttagtg  aagggttgtt       840
ccgatacttc  tccacattca  gtcatagatg  ggcagctttg  ttatcatgaa  gagacggaaa       900
cgggcattaa  gggttaaccg  ccaaattata  taaagacaac  atgtccccag  tttaaagttt       960
ttctttccta  ttcttgtatc  ctgagtgacc  gttgtgttta  ataacaag    ttcgttttaa      1020 cttaagacca  aaaccagtta  caacaaatta  taaccctct   aaacactaaa  gttcactctt      1080
atcaaactat  caaacatcaa  aa                                                  1102

<210> SEQ ID NO 12
<211> LENGTH: 358
<212> TYPE: DNA
<213> ORGANISM: Pichia pastoris

<400> SEQUENCE: 12
tgagataaca  gagttgggta  actagagaga  ataatagacg  tatgcatgat  tactacacaa        60
cggatgtcgc  actctttcct  tagttaaaac  tatcatccaa  tcacaagatg  cgggctggaa       120
agacttgctc  ccgaaggata  atcttctgct  tctatctccc  ttcctcatat  ggtttcgcag       180
ggctcatgcc  ccttcttcct  tcgaactgcc  cgatgaggaa  gtccttagcc  tatcaaagaa       240
ttcgggacca  tcatcgattt  ttagagcctt  acctgatcgc  aatcaggatt  tcactactca       300
tataaataca  tcgctcaaag  ctccaacttt  gcttgttcat  acaattcttg  atattcac         358

<210> SEQ ID NO 13
<211> LENGTH: 6688
<212> TYPE: DNA
<213> ORGANISM: artificial
<220> FEATURE:
<223> OTHER INFORMATION: Plasmid promoter sequence

<400> SEQUENCE: 13
attctggccc  ttgcacctga  tcgcgaaggt  ggaaatggca  gaaggatcag  cctggacgaa        60
gcaaccagtt  ccaactgcta  agtaaagaag  atgctagacg  aaggagactt  cagaggtgaa       120
aagtttgcaa  gaagagagct  gcgggaaata  aattttcaat  ttaaggactt  gagtgcgtcc       180
atattcgtgt  acgtgtccaa  ctgttttcca  ttacctaaga  aaaacataaa  gattaaaaag       240
ataaacccaa  tcgggaaact  ttagcgtgcc  gtttcggatt  ccgaaaaact  tttggagcgc       300
cagatgacta  tggaaagagg  agtgtaccaa  aatggcaagt  cggggctac   tcaccgata        360 gccaatacat  tctctaggaa  ccagggatga  atccaggttt  ttgttgtcac  ggtaggtcaa       420
gcattcactt  cttaggaata  tctcgttgaa  agctacttga  atcccattg   ggtgcggaac       480 cagcttctaa  ttaaatagtt  cgatgatgtt  ctctaagtgg  gactctacgg  ctcaaacttc       540
tacacagcat  catcttagta  gtcccttccc  aaaacaccat  tctaggtttc  ggaacgtaac       600
gaaacaatgt  tcctctcttc  acattgggcc  gttactctag  ccttccgaag  aaccaataaa       660
agggaccggc  tgaaacgggt  gtggaaactc  ctgtccagtt  tatggcaaag  gctacagaaa       720
tcccaatctt  gtcgggatgt  tgctcctccc  aaacgccata  ttgtactgca  gttggtgcgc       780
```

```
attttaggga aaatttaccc cagatgtcct gattttcgag ggctacccc aactccctgt      840 gcttatactt agtctaattc tattcagtgt gctgacctac acgtaatgat gtcgtaaccc      900
agttaaatgg ccgaaaaact atttaagtaa gtttatttct cctccagatg agactctcct      960
tcttttctcc gctagttatc aaactataaa cctatttac ctcaaatacc tccaacatca     1020
cccacttaaa cacggccgaa ttcataatga gatttccttc aattttact gcagttttat     1080 tcgcagcatc ctccgcatta gctgctccag tcaacactac aacagaagat gaaacggcac     1140
aaattccggc tgaagctgtc atcggttact cagatttaga aggggatttc gatgttgctg     1200
ttttgccatt ttccaacagc acaaataacg ggttattgtt tataaatact actattgcca     1260
gcattgctgc taaagaagaa ggggtatctc tcgagaaaag agaggctgaa gctttaatta     1320
actgggccgc gaattaattc gccttagaca tgactgttcc tcagttcaag ttgggcactt     1380
acgagaagac cggtcttgct agattctaat caagaggatg tcagaatgcc atttgcctga     1440
gagatgcagg cttcattttt gatacttttt tatttgtaac ctatatagta taggatttt      1500 tttgtcattt tgtttcttct cgtacgagct tgctcctgat cagcctatct cgcagctgat     1560
gaatatcttg tggtaggggt ttgggaaaat cattcgagtt tgatgttttt cttggtattt     1620
cccactcctc ttcagagtac agaagattaa gtgagacgtt cgtttgtgca agcttatcga     1680
taagctttaa tgcggtagtt tatcacagtt aaattgctaa cgcagtcagg caccgtgtat     1740
gaaatctaac aatgcgctca tcgtcatcct cggcaccgtc accctggatg ctgtaggcat     1800
aggcttggtt atgccggtac tgccgggcct cttgcgggat atcgtccatt ccgacagcat     1860
cgccagtcac tatggcgtgc tgctaggtac aacttgagca agttgtcgat cagctcctca     1920
aattggtcct ctgtaacgga tgactcaact tgcacattaa cttgaagctc agtcgattga     1980
gtgaacttga tcaggttgtg cagctggtca gcagcatagg gaaacacggc ttttcctacc     2040
aaactcaagg aattatcaaa ctctgcaaca cttgcgtatg caggtagcaa gggaaatgtc     2100
atacttgaag tcggacagtg agtgtagtct tgagaaattc tgaagccgta ttttttattat     2160 cagtgagtca gtcatcagga gatcctctac gccggacgca tcgtggccga cctgcagggg     2220
gggggggggc gctgaggtct gcctcgtgaa gaaggtgttg ctgactcata ccagctgaat     2280
cgccccatca tccagccaga aagtgaggga gccacggttg atgagagctt tgttgtaggt     2340
ggaccagttg gtgattttga acttttgctt tgccacggaa cggtctgcgt tgtcgggaag     2400
atgcgtgatc tgatccttca actcagcaaa agttcgattt attcaacaaa gccgccgtcc     2460
cgtcaagtca gcgtaatgct ctgccagtgt acaaccaat taaccaattc tgattagaaa     2520
aactcatcga gcatcaaatg aaactgcaat ttattcatat caggattatc aataccatat     2580
ttttgaaaaa gccgtttctg taatgaagga gaaaactcac cgaggcagtt ccataggatg     2640
gcaagatcct ggtatcggtc tgcgattccg actcgtccaa catcaataca acctattaat     2700
ttcccctcgt caaaaataag gttatcaagt gagaaatcac catgagtgac gactgaatcc     2760
ggtgagaatg gcaaaagctt atgcatttct ttccagactt gttcaacagg ccagccatta     2820
cgctcgtcat caaaatcact cgcatcaacc aaaccgttat tcattcgtga ttgcgcctga     2880
gcgagacgaa atacgcgatc gctgttaaaa ggacaattac aaacaggaat cgaatgcaac     2940
cggcgcagga acactgccag cgcatcaaca atattttcac ctgaatcagg atattcttct     3000
aatacctgga atgctgtttt cccggggatc gcagtggtga gtaaccatgc atcatcagga     3060
gtacggataa aatgcttgat ggtcggaaga ggcataaatt ccgtcagcca gtttagtctg     3120
```

```
accatctcat ctgtaacatc attggcaacg ctacctttgc catgtttcag aaacaactct    3180
ggcgcatcgg gcttcccata caatcgatag attgtcgcac ctgattgccc gacattatcg    3240
cgagcccatt tatacccata taaatcagca tccatgttgg aatttaatcg cggcctcgag    3300
caagacgttt cccgttgaat atggctcata acacccttg tattactgtt tatgtaagca     3360
gacagtttta ttgttcatga tgatatattt ttatcttgtg caatgtaaca tcagagattt    3420
tgagacacaa cgtggctttc ccccccccc ctgcaggtcg gcatcaccgg cgccacaggt     3480
gcggttgctg gcgcctatat cgccgacatc accgatgggg aagatcgggc tcgccacttc    3540
gggctcatga gcgcttgttt cggcgtgggt atggtggcag ccccgtggc cgggggactg     3600 ttgggcgcca tctccttgca tgcaccattc cttgcggcgg cggtgctcaa cggcctcaac    3660
ctactactgg gctgcttcct aatgcaggag tcgcataagg gagagcgtcg agtatctatg    3720
attggaagta tgggaatggt gatacccgca ttcttcagtg tcttgaggtc tcctatcaga    3780
ttatgcccaa ctaaagcaac cggaggagga gatttcatgg taaatttctc tgacttttgg    3840
tcatcagtag actcgaactg tgagactatc tcggttatga cagcagaaat gtccttcttg    3900
gagacagtaa atgaagtccc accaataaag aaatccttgt tatcaggaac aaacttcttg    3960
tttcgaactt tttcggtgcc ttgaactata aatgtgagg tggatatgtc gggtaggaat     4020
ggagcgggca aatgcttacc ttctggacct tcaagaggta tgtagggttt gtagatactg    4080
atgccaactt cagtgacaac gttgctattt cgttcaaacc attccgaatc cagagaaatc    4140
aaagttgttt gtctactatt gatccaagcc agtgcggtct tgaaactgac aatagtgtgc    4200
tcgtgttttg aggtcatctt tgtatgaata aatctagtct ttgatctaaa taatcttgac    4260
gagccaaggc gataaatacc caaatctaaa actctttta aacgttaaaa ggacaagtat     4320
gtctgcctgt attaaacccc aaatcagctc gtagtctgat cctcatcaac ttgaggggca    4380
ctatcttgtt ttagagaaat ttgcggagat gcgatatcga gaaaaggta cgctgatttt    4440 aaacgtgaaa tttatctcaa gatctctgcc tcgcgcgttt cggtgatgac ggtgaaaacc    4500
tctgacacat gcagctcccg gagacggtca cagcttgtct gtaagcggat gccgggagca    4560
gacaagcccg tcagggcgcg tcagcgggtg ttggcgggtg tcggggcgca gccatgaccc    4620
agtcacgtag cgatagcgga gtgtatactg gcttaactat gcggcatcag agcagattgt    4680
actgagagtg caccatatgc ggtgtgaaat accgcacaga tgcgtaagga gaaataccg     4740 catcaggcgc tcttccgctt cctcgctcac tgactcgctg cgctcggtcg ttcggctgcg    4800
gcgagcggta tcagctcact caaaggcggt aatacggtta ccacagaat caggggataa     4860 cgcaggaaag aacatgtgag caaaaggcca gcaaaggcc aggaaccgta aaaaggccgc      4920
gttgctggcg ttttccata ggctccgccc ccctgacgag catcacaaaa atcgacgctc      4980
aagtcagagg tggcgaaacc cgacaggact ataaagatac caggcgtttc ccctggaag     5040 ctccctcgtg cgctctcctg ttccgaccct gccgcttacc ggatacctgt ccgcctttct    5100
cccttcggga agcgtggcgc tttctcaatg ctcacgctgt aggtatctca gttcggtgta    5160
ggtcgttcgc tccaagctgg gctgtgtgca cgaaccccc gttcagcccg accgctgcgc     5220
cttatccggt aactatcgtc ttgagtccaa cccggtaaga cacgacttat cgccactggc    5280
agcagccact ggtaacagga ttagcagagc gaggtatgta ggcggtgcta cagagttctt    5340
gaagtggtgg cctaactacg gctacactag aaggacagta tttggtatct gcgctctgct    5400
gaagccagtt accttcggaa aaagagttgg tagctcttga tccggcaaac aaaccaccgc    5460
tggtagcggt ggtttttttg tttgcaagca gcagattacg cgcagaaaaa aaggatctca    5520
```

```
agaagatcct tgatctttt ctacggggtc tgacgctcag tggaacgaaa actcacgtta     5580
agggattttg gtcatgagat tatcaaaaag gatcttcacc tagatccttt taaattaaaa    5640
atgaagtttt aaatcaatct aaagtatata tgagtaaact tggtctgaca gttaccaatg   5700
cttaatcagt gaggcaccta tctcagcgat ctgtctattt cgttcatcca tagttgcctg   5760
actccccgtc gtgtagataa ctacgatacg ggagggctta ccatctggcc ccagtgctgc   5820
aatgataccg cgagacccac gctcaccggc tccagattta tcagcaataa accagccagc   5880
cggaagggcc gagcgcagaa gtggtcctgc aactttatcc gcctccatcc agtctattaa   5940
ttgttgccgg gaagctagag taagtagttc gccagttaat agtttgcgca acgttgttgc   6000
cattgctgca ggcatcgtgg tgtcacgctc gtcgtttggt atggcttcat tcagctccgg   6060
ttcccaacga tcaaggcgag ttacatgatc ccccatgttg tgcaaaaaag cggttagctc   6120
cttcggtcct ccgatcgttg tcagaagtaa gttggccgca gtgttatcac tcatggttat   6180
ggcagcactg cataattctc ttactgtcat gccatccgta agatgctttt ctgtgactgg   6240
tgagtactca accaagtcat tctgagaata gtgtatgcgg cgaccgagtt gctcttgccc   6300
ggcgtcaaca cgggataata ccgcgccaca tagcagaact ttaaaagtgc tcatcattgg   6360
aaaacgttct cggggcgaa aactctcaag gatcttaccg ctgttgagat ccagttcgat   6420
gtaacccact cgtgcaccca actgatcttc agcatctttt actttcacca gcgtttctgg   6480
gtgagcaaaa acaggaaggc aaaatgccgc aaaaaaggga ataagggcga cacggaaatg   6540
ttgaatactc atactcttcc tttttcaata ttattgaagc atttatcagg gttattgtct   6600
catgagcgga tacatatttg aatgtattta gaaaaataaa caaatagggg ttccgcgcac   6660
atttccccga aaagtgccac ctgacgtc                                     6688

<210> SEQ ID NO 14
<211> LENGTH: 159
<212> TYPE: DNA
<213> ORGANISM: human

<400> SEQUENCE: 14
aatagtgact ctgaatgccc tttgtcccat gacggatact gtcttcacga cggcgtttgt     60
atgtatatcg aggcactaga taagtatgca tgtaactgcg tagtaggata cattggagaa    120
cgttgccaat accgtgattt gaagtggtgg gagttgcgt                           159

<210> SEQ ID NO 15
<211> LENGTH: 666
<212> TYPE: DNA
<213> ORGANISM: human

<400> SEQUENCE: 15
tggacgggcg aggactcggc ggagcccaac tctgactcgg cggagtggat ccgagacatg     60
tacgccaagg tcacggagat ctggcaggag gtcatgcagc ggcggacga cgacggcgcg    120 ctccacgccg cctgccaggt gcagccgtcg gccacgctgg acgccgcgca gccccgggtg   180
accggcgtcg tcctcttccg gcagcttgcg ccccgcgcca agctcgacgc cttcttcgcc   240
ctggagggct tcccgaccga gccgaacagc tccagccgcg ccatccacgt gcaccagttc   300
ggggacctga gccagggctg cgagtccacc gggccccact acaacccgct ggccgtgccg   360 caccccgcagc acccgggcga cttcggcaac ttcgcggtcc gcgacggcag cctctggagg   420
taccgcgccg gcctggccgc ctcgctcgcg ggcccgcact ccatcgtggg ccgggccgtg   480
```

```
gtcgtccacg ctggcgagga cgacctgggc cgcggcggta accaggccag cgtggagaac    540
gggaacgcgg gccggcggct ggcctgctgc gtggtgggcg tgtgcgggcc cgggctctgg    600
gagcgccagg cgcgggagca ctcagagcgc aagaagcggc ggcgcgagag cgagtgcaag    660
gccgcc                                                               666

<210> SEQ ID NO 16
<211> LENGTH: 2076
<212> TYPE: DNA
<213> ORGANISM: human

<400> SEQUENCE: 16
ggccgtagga gaaggagtgt tcagtggtgc gccgtatccc aacccgaggc cacaaaatgc     60
ttccaatggc aaaggaatat gagaaaagtg cgtggccctc ctgtcagctg cataaagaga    120
gactccccca tccagtgtat ccaggccatt gcggaaaaca gggccgatgc tgtgacccct    180
gatggtggtt tcatatacga ggcaggcctg gccccctaca aactgcgacc tgtagcggcg    240
gaagtctacg ggaccgaaag acagccacga actcactatt atgccgtggc tgtggtgaag    300
aagggcggca gctttcagct gaacgaactg caaggtctga gtcctgcca cacaggcctt    360 cgcaggaccg ctggatggaa tgtccctata gggacacttc gtccattctt gaattggacg    420
ggtccacctg agcccattga ggcagctgtg gccaggttct tctcagccag ctgtgttccc    480
ggtgcagata aaggacagtt ccccaacctg tgtcgcctgt gtgcggggac aggggaaaac    540
aaatgtgcct ctcctccca ggaaccgtac ttcagctact ctggtgcctt caagtgtctg    600
agagacgggg ctggagacgt ggcttttatc agagagagca cagtgtttga ggacctgtca    660
gacgaggctg aaagggacga gtatgagtta ctctgcccag acaacactcg gaagccagtg    720
gacaagttca aagactgcca tctggcccgg gtccccttctc atgccgttgt ggcacgaagt    780
gtgaatggca aggaggatgc catctggaat cttctccgcc aggcacagga aaagtttgga    840
aaggacaagt caccgaaatt ccagctcttt ggctccccta gtgggcagaa agatctgctg    900
ttcaaggact ctgccattgg gttttcgagg gtgcccccga ggatagattc tgggctgtac    960
cttggctccg gctacttcac tgccatccag aacttgagga aaagtgagga ggaagtggct   1020
gcccggcgtg cgcgggtcgt gtggtgtgcg gtgggcgagc aggagctgcg caagtgtaac   1080
cagtggagtg gcttgagcga aggcagcgtg acctgctcct cggcctccac cacagaggac   1140
tgcatcgccc tggtgctgaa aggagaagct gatgccatga gtttggatgg aggatatgtg   1200
tacactgcag gcaaatgtgg tttggtgcct gtcctggcag agaactacaa atcccaacaa   1260
agcagtgacc ctgatcctaa ctgtgtggat agacctgtgg aaggatatct tgctgtggcg   1320
gtggttagga gatcagacac tagccttacc tggaactctg tgaaaggcaa gaagtcctgc   1380
cacaccgccg tggacaggac tgcaggctgg aatatcccca tgggcctgct cttcaaccag   1440
acgggctcct gcaaatttga tgaatatttc agtcaaagct gtgcccctgg gtctgacccg   1500
agatctaatc tctgtgctct gtgtattggc gacgagcagg tgagaataa gtgcgtgccc   1560 aacagcaacg agagatacta cggctacact ggggctttcc ggtgcctggc tgagaatgct   1620
ggagacgttg catttgtgaa agatgtcact gtcttgcaga acactgatgg aaataacaat   1680
gaggcatggg ctaaggattt gaagctggca gactttgcgc tgctgtgcct cgatggcaaa   1740
cggaagcctg tgactgaggc tagaagctgc catcttgcca tggccccgaa tcatgccgtg   1800
gtgtctcgga tggataaggt ggaacgcctg aaacaggtgt tgctccacca acaggctaaa   1860
tttgggagaa atggatctga ctgcccggac aagttttgct tattccagtc tgaaaccaaa   1920
```

```
aaccttctgt tcaatgacaa cactgagtgt ctggccagac tccatggcaa acaacatat    1980 gaaaaatatt tgggaccaca gtatgtcgca ggcattacta atctgaaaaa gtgctcaacc    2040
tcccccctcc tggaagcctg tgagttcctc aggaag                              2076
```

```
<210> SEQ ID NO 17
<211> LENGTH: 53
<212> TYPE: PRT
<213> ORGANISM: human

<400> SEQUENCE: 17
```

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

```
<210> SEQ ID NO 18
<211> LENGTH: 222
<212> TYPE: PRT
<213> ORGANISM: human

<400> SEQUENCE: 18
```

Trp Thr Gly Glu Asp Ser Ala Glu Pro Asn Ser Asp Ser Ala Glu Trp
1               5                   10                  15

Ile Arg Asp Met Tyr Ala Lys Val Thr Glu Ile Trp Gln Glu Val Met
            20                  25                  30

Gln Arg Arg Asp Asp Gly Ala Leu His Ala Ala Cys Gln Val Gln
        35                  40                  45

Pro Ser Ala Thr Leu Asp Ala Ala Gln Pro Arg Val Thr Gly Val Val
    50                  55                  60

Leu Phe Arg Gln Leu Ala Pro Arg Ala Lys Leu Asp Ala Phe Phe Ala
65                  70                  75                  80

Leu Glu Gly Phe Pro Thr Glu Pro Asn Ser Ser Arg Ala Ile His
            85                  90                  95

Val His Gln Phe Gly Asp Leu Ser Gln Gly Cys Glu Ser Thr Gly Pro
        100                 105                 110

His Tyr Asn Pro Leu Ala Val Pro His Pro Gln His Pro Gly Asp Phe
    115                 120                 125

Gly Asn Phe Ala Val Arg Asp Gly Ser Leu Trp Arg Tyr Arg Ala Gly
    130                 135                 140

Leu Ala Ala Ser Leu Ala Gly Pro His Ser Ile Val Gly Arg Ala Val
145                 150                 155                 160

Val Val His Ala Gly Glu Asp Asp Leu Gly Arg Gly Gly Asn Gln Ala
            165                 170                 175

Ser Val Glu Asn Gly Asn Ala Gly Arg Arg Leu Ala Cys Cys Val Val
        180                 185                 190

Gly Val Cys Gly Pro Gly Leu Trp Glu Arg Gln Ala Arg Glu His Ser
    195                 200                 205

Glu Arg Lys Lys Arg Arg Glu Ser Glu Cys Lys Ala Ala
    210                 215                 220

```
<210> SEQ ID NO 19
```

<211> LENGTH: 692
<212> TYPE: PRT
<213> ORGANISM: human

<400> SEQUENCE: 19

| | | | | | | | | | | | | | | |
|---|---|---|---|---|---|---|---|---|---|---|---|---|---|---|
| Gly | Arg | Arg | Arg | Arg | Ser | Val | Gln | Trp | Cys | Ala | Val | Ser | Gln | Pro | Glu |
| 1 | | | | 5 | | | | | 10 | | | | | 15 | |
| Ala | Thr | Lys | Cys | Phe | Gln | Trp | Gln | Arg | Asn | Met | Arg | Lys | Val | Arg | Gly |
| | | | 20 | | | | | 25 | | | | | 30 | | |
| Pro | Pro | Val | Ser | Cys | Ile | Lys | Arg | Asp | Ser | Pro | Ile | Gln | Cys | Ile | Gln |
| | | 35 | | | | | 40 | | | | | 45 | | | |
| Ala | Ile | Ala | Glu | Asn | Arg | Ala | Asp | Ala | Val | Thr | Leu | Asp | Gly | Gly | Phe |
| 50 | | | | | 55 | | | | | 60 | | | | | |
| Ile | Tyr | Glu | Ala | Gly | Leu | Ala | Pro | Tyr | Lys | Leu | Arg | Pro | Val | Ala | Ala |
| 65 | | | | | 70 | | | | 75 | | | | | | 80 |
| Glu | Val | Tyr | Gly | Thr | Glu | Arg | Gln | Pro | Arg | Thr | His | Tyr | Tyr | Ala | Val |
| | | | | 85 | | | | | 90 | | | | | 95 | |
| Ala | Val | Val | Lys | Lys | Gly | Gly | Ser | Phe | Gln | Leu | Asn | Glu | Leu | Gln | Gly |
| | | | 100 | | | | | 105 | | | | | 110 | | |
| Leu | Lys | Ser | Cys | His | Thr | Gly | Leu | Arg | Arg | Thr | Ala | Gly | Trp | Asn | Val |
| | | 115 | | | | | 120 | | | | | 125 | | | |
| Pro | Ile | Gly | Thr | Leu | Arg | Pro | Phe | Leu | Asn | Trp | Thr | Gly | Pro | Pro | Glu |
| | 130 | | | | | 135 | | | | | 140 | | | | |
| Pro | Ile | Glu | Ala | Ala | Val | Ala | Arg | Phe | Phe | Ser | Ala | Ser | Cys | Val | Pro |
| 145 | | | | | 150 | | | | | 155 | | | | | 160 |
| Gly | Ala | Asp | Lys | Gly | Gln | Phe | Pro | Asn | Leu | Cys | Arg | Leu | Cys | Ala | Gly |
| | | | | 165 | | | | | 170 | | | | | 175 | |
| Thr | Gly | Glu | Asn | Lys | Cys | Ala | Phe | Ser | Ser | Gln | Glu | Pro | Tyr | Phe | Ser |
| | | | 180 | | | | | 185 | | | | | 190 | | |
| Tyr | Ser | Gly | Ala | Phe | Lys | Cys | Leu | Arg | Asp | Gly | Ala | Gly | Asp | Val | Ala |
| | | 195 | | | | | 200 | | | | | 205 | | | |
| Phe | Ile | Arg | Glu | Ser | Thr | Val | Phe | Glu | Asp | Leu | Ser | Asp | Glu | Ala | Glu |
| | 210 | | | | | 215 | | | | | 220 | | | | |
| Arg | Asp | Glu | Tyr | Glu | Leu | Leu | Cys | Pro | Asp | Asn | Thr | Arg | Lys | Pro | Val |
| 225 | | | | | 230 | | | | | 235 | | | | | 240 |
| Asp | Lys | Phe | Lys | Asp | Cys | His | Leu | Ala | Arg | Val | Pro | Ser | His | Ala | Val |
| | | | | 245 | | | | | 250 | | | | | 255 | |
| Val | Ala | Arg | Ser | Val | Asn | Gly | Lys | Glu | Asp | Ala | Ile | Trp | Asn | Leu | Leu |
| | | | 260 | | | | | 265 | | | | | 270 | | |
| Arg | Gln | Ala | Gln | Glu | Lys | Phe | Gly | Lys | Asp | Lys | Ser | Pro | Lys | Phe | Gln |
| | | 275 | | | | | 280 | | | | | 285 | | | |
| Leu | Phe | Gly | Ser | Pro | Ser | Gly | Gln | Lys | Asp | Leu | Leu | Phe | Lys | Asp | Ser |
| | 290 | | | | | 295 | | | | | 300 | | | | |
| Ala | Ile | Gly | Phe | Ser | Arg | Val | Pro | Pro | Arg | Ile | Asp | Ser | Gly | Leu | Tyr |
| 305 | | | | | 310 | | | | | 315 | | | | | 320 |
| Leu | Gly | Ser | Gly | Tyr | Phe | Thr | Ala | Ile | Gln | Asn | Leu | Arg | Lys | Ser | Glu |
| | | | | 325 | | | | | 330 | | | | | 335 | |
| Glu | Glu | Val | Ala | Ala | Arg | Arg | Ala | Arg | Val | Val | Trp | Cys | Ala | Val | Gly |
| | | | 340 | | | | | 345 | | | | | 350 | | |
| Glu | Gln | Glu | Leu | Arg | Lys | Cys | Asn | Gln | Trp | Ser | Gly | Leu | Ser | Glu | Gly |
| | | 355 | | | | | 360 | | | | | 365 | | | |
| Ser | Val | Thr | Cys | Ser | Ser | Ala | Ser | Thr | Thr | Glu | Asp | Cys | Ile | Ala | Leu |
| | 370 | | | | | 375 | | | | | 380 | | | | |
| Val | Leu | Lys | Gly | Glu | Ala | Asp | Ala | Met | Ser | Leu | Asp | Gly | Gly | Tyr | Val |

```
385                 390                 395                 400
Tyr Thr Ala Gly Lys Cys Gly Leu Val Pro Val Leu Ala Glu Asn Tyr
                405                 410                 415
Lys Ser Gln Gln Ser Ser Asp Pro Asp Pro Asn Cys Val Asp Arg Pro
                420                 425                 430
Val Glu Gly Tyr Leu Ala Val Ala Val Val Arg Arg Ser Asp Thr Ser
                435                 440                 445
Leu Thr Trp Asn Ser Val Lys Gly Lys Ser Cys His Thr Ala Val
        450                 455                 460
Asp Arg Thr Ala Gly Trp Asn Ile Pro Met Gly Leu Leu Phe Asn Gln
465                 470                 475                 480
Thr Gly Ser Cys Lys Phe Asp Glu Tyr Phe Ser Gln Ser Cys Ala Pro
                485                 490                 495
Gly Ser Asp Pro Arg Ser Asn Leu Cys Ala Leu Cys Ile Gly Asp Glu
                500                 505                 510
Gln Gly Glu Asn Lys Cys Val Pro Asn Ser Asn Glu Arg Tyr Tyr Gly
                515                 520                 525
Tyr Thr Gly Ala Phe Arg Cys Leu Ala Glu Asn Ala Gly Asp Val Ala
                530                 535                 540
Phe Val Lys Asp Val Thr Val Leu Gln Asn Thr Asp Gly Asn Asn Asn
545                 550                 555                 560
Glu Ala Trp Ala Lys Asp Leu Lys Leu Ala Asp Phe Ala Leu Leu Cys
                565                 570                 575
Leu Asp Gly Lys Arg Lys Pro Val Thr Glu Ala Arg Ser Cys His Leu
                580                 585                 590
Ala Met Ala Pro Asn His Ala Val Val Ser Arg Met Asp Lys Val Glu
                595                 600                 605
Arg Leu Lys Gln Val Leu Leu His Gln Gln Ala Lys Phe Gly Arg Asn
                610                 615                 620
Gly Ser Asp Cys Pro Asp Lys Phe Cys Leu Phe Gln Ser Glu Thr Lys
625                 630                 635                 640
Asn Leu Leu Phe Asn Asp Asn Thr Glu Cys Leu Ala Arg Leu His Gly
                645                 650                 655
Lys Thr Thr Tyr Glu Lys Tyr Leu Gly Pro Gln Tyr Val Ala Gly Ile
                660                 665                 670
Thr Asn Leu Lys Lys Cys Ser Thr Ser Pro Leu Leu Glu Ala Cys Glu
                675                 680                 685
Phe Leu Arg Lys
    690

<210> SEQ ID NO 20
<211> LENGTH: 651
<212> TYPE: DNA
<213> ORGANISM: SARS-CoV-2

<400> SEQUENCE: 20
gtacagccta cagaaagtat tgtccgtttc cctaatatca ccaatttatg ccctttggt       60 gaagtcttca atgccaccag attcgcctcc gtatatgcct ggaaccgtaa gagaatcagt     120
aattgcgtgg ccgattattc tgtgttgtat aatagtgcct ccttctccac cttcaagtgt     180
tatggcgtgt cccctactaa gctgaatgac ttatgtttta ccaatgttta tgcagactca     240
ttcgtcatcc gtggagatga agtccgtcaa attgccccg acagacagg aaaaatcgcc       300 gactataatt ataaactgcc tgatgacttc accggatgtg tcatcgcatg gaatagtaat     360
```

```
aatttagatt caaaagtagg aggaaattat aattatcttt accgtctgtt tagaaaatca    420
aacttgaaac cattcgagag agatatttcc acagagatct accaggcagg atccacccct    480
tgcaatggag tcgaaggatt caattgctat tttcctctgc agtcttatgg atttcagcct    540
acaaatggag tcggatacca accttataga gtcgtggtct taagtttcga gttgcttcac    600
gccgtcgcca cagtgtgcgg acctaaaaag tcaacaaatt tagtcaagaa t             651
```

<210> SEQ ID NO 21
<211> LENGTH: 217
<212> TYPE: PRT
<213> ORGANISM: SARS-CoV-2

<400> SEQUENCE: 21

```
Val Gln Pro Thr Glu Ser Ile Val Arg Phe Pro Asn Ile Thr Asn Leu
1               5                   10                  15

Cys Pro Phe Gly Glu Val Phe Asn Ala Thr Arg Phe Ala Ser Val Tyr
            20                  25                  30

Ala Trp Asn Arg Lys Arg Ile Ser Asn Cys Val Ala Asp Tyr Ser Val
        35                  40                  45

Leu Tyr Asn Ser Ala Ser Phe Ser Thr Phe Lys Cys Tyr Gly Val Ser
50                  55                  60

Pro Thr Lys Leu Asn Asp Leu Cys Phe Thr Asn Val Tyr Ala Asp Ser
65                  70                  75                  80

Phe Val Ile Arg Gly Asp Glu Val Arg Gln Ile Ala Pro Gly Gln Thr
                85                  90                  95

Gly Lys Ile Ala Asp Tyr Asn Tyr Lys Leu Pro Asp Asp Phe Thr Gly
            100                 105                 110

Cys Val Ile Ala Trp Asn Ser Asn Asn Leu Asp Ser Lys Val Gly Gly
        115                 120                 125

Asn Tyr Asn Tyr Leu Tyr Arg Leu Phe Arg Lys Ser Asn Leu Lys Pro
130                 135                 140

Phe Glu Arg Asp Ile Ser Thr Glu Ile Tyr Gln Ala Gly Ser Thr Pro
145                 150                 155                 160

Cys Asn Gly Val Glu Gly Phe Asn Cys Tyr Phe Pro Leu Gln Ser Tyr
                165                 170                 175

Gly Phe Gln Pro Thr Asn Gly Val Gly Tyr Gln Pro Tyr Arg Val Val
            180                 185                 190

Val Leu Ser Phe Glu Leu Leu His Ala Val Ala Thr Val Cys Gly Pro
        195                 200                 205

Lys Lys Ser Thr Asn Leu Val Lys Asn
210                 215
```

METHOD FOR METHANOL FREE CULTURING OF METHYLOTROPHIC YEAST FOR THE BIOSYNTHESIS OF ADDED VALUE PRODUCTS

PRIOR APPLICATION INFORMATION

The instant application claims the benefit of U.S. Provisional Application 63/214,376, filed Jun. 24, 2021 and entitled "Method for methanol free culturing of methylotrophic yeast for the biosynthesis of added value products", the entire contents of which are incorporated herein by reference for all purposes.

FIELD OF THE INVENTION

The present invention relates to the field of culturing/fermentation of methylotrophic yeast (e.g. *Pichia pastoris* or *Komagataella phaffii*) to produce value added products like recombinant proteins or small molecule compounds.

BACKGROUND

Methylotrophic yeast such as *Pichia pastoris*, also known as *Komagataella phaffii*, is widely used as a host organism for recombinant protein production. The ability of this yeast to use the cheap substrate methanol as sole carbon source, its high cell density fermentation capability, its secretory machinery and powerful and tightly regulated promoters have resulted in its extensive application in biotechnology. Albeit there are strong constitutive promoters like GAP (Glyceraldehyde-3-P dehydrogenase) promoter, TEF1 promoter (Translation elongation factor), inducible promoters like AOX1 promoter (Alcohol oxidase) have advantages for production purposes as they allow biomass growth without product formation. Thus, cells are not stressed by the accumulation of recombinant products during growth, enabling better process control. AOX1 gene in *P. pastoris* cells is dramatically upregulated in response to methanol, whereas it stays tightly repressed when glucose or glycerol or any other fermentable carbon source is in the media. Therefore, amongst all inducible promoters, AOX1 promoter is most abundantly used. A typical bioprocess driven by any inducible promoter comprises biomass growth on glucose or glycerol (batch) phase followed by induction of expression followed by recombinant protein(s)/compound(s) production upon switching to methanol (fed-batch and induction phase).

In response to different carbon sources, all inducible promoters, including AOX 1, have three regulated states of gene expression: catabolite repression (or just repression), derepression, and activation (induction). For AOX1 promoters, these states are well described, unlike for the other inducible promoters described herein. When glycerol or glucose or ethanol or any other fermentable carbon source is in abundance in the culture media, AOX1 promoter is completely repressed. When those carbon sources are depleted, the AOX1 promoter is derepressed, which means it is activated at roughly 2-5% of its methanol induction level. AOX1 promoter can also be de-repressed when culture grows on so-called non-repressible carbon sources (e.g. sorbitol, mannitol, alanine or trehalose). When the culture starts to consume methanol as a carbon source, with or without non-repressible carbon sources, AOX1 promoter, and the other listed promoters are fully activated (i.e. induced), Although methanol is widely used as an inducer for the AOX1 driven induction system, many shortcomings of using methanol in the fermentation process (e.g. it's flammability and toxicity) greatly limits the feasibility of this system at large industrial scales. Recently it was shown that the salts of formic acid (formates) can induce AOX1 promoter almost as well as methanol. However, it still remains unknown whether other native promoters discussed herein can be induced by formic acid or formates. Also, it has not been determined if formates or formic acid can be used as an inducer in combination with non-repressible carbon sources.

SUMMARY OF THE INVENTION

The safety aspect of the fermentation/culturing process is supposed to be the subject of particular attention. In this respect, the storage of large volumes of hazardous and flammable methanol at industrial facilities is highly undesirable. Apart from the fact that it makes the fermentation process dangerous and environmentally un-friendly, the expenses for extra safety measures can add an extra 15% to total production cost. Furthermore, methanol metabolism leads to an increase in heat evolution, which is not technologically favorable because the culturing consumes a lot of energy to chill the bioreactors. Another downside of methanol metabolism is a high oxygen consumption by the culture, which is considered as a hazard because it requires a production facility with a high oxygen capacity. Thus, to make the bioprocess safer and cheaper, it is highly advantageous to exclude methanol from the culturing process, while maintaining or even surpassing the high level of expression of the conventional AOX1 or other MUT pathway inducible genes. There are some currently used approaches based on genetic modifications of yeast, but none allows for complete avoidance of methanol use with already designed strains.

Described herein is a culturing method that combines the use of the previously described alternative inducing agent, salts of formic acid (formates) or formic acid together with any suitable non-repressing feeding substrate, such as sorbitol, mannitol, trehalose or alanine. Also described is the use of salts of formic acid (formates) or formic acid as an alternative to methanol inducer with or without non-repressing carbon sources for the following promoters: the $NAD^+$-dependent formate dehydrogenase (FDH) promoter (one example of which is provided as SEQ ID NO: 1), the alcohol oxidase 2 (AOX2) promoter (one example of which is provided as SEQ ID NO:2), peroxin Pex14p (PEX14) promoter (one example of which is provided as SEQ ID NO:3), the dihydroxyacetone kinase (DAK) promoter (one example of which is provided as SEQ NO:ID 5), the dihydroxyacetone synthase 1,2 (DAS1,2) promoter (example of which are provided as SEQ ID NO:10 SEQ ID NO:11 respectively), the formyl-glutathione dehydrogenase (FGH) promoter (one example of which is provided as SEQ ID NO:4), the formaldehyde dehydrogenase 1 (FLD1) promoter (one example of which is provided as SEQ ID NO:12), the Fructose 1,6-bisphosphate aldolase (FBA) promoter (one example of which is provided as SEQ ID NO:6), the Peroxisomal membrane signal receptor PTS1 (PEX5) promoter (one example of which is provided as SEQ ID NO:7), the alcohol dehydrogenase 2 (ADH2) promoter (one example of which is provided as SEQ ID NO:8), and a catalase (CAT) promoter (one example of which is provided as SEQ ID NO:9).

As will be apparent to those of skill in the art, the promoter sequences provided in SEQ ID NOs: 1-12 are intended for illustrative purposes only and suitable variants of these may be used within the invention, depending on the host cell used.

As will be appreciated by one of skill in the art, finding a new compound that is capable of induction of certain promoter(s) is not obvious from the perspective that it needs to be demonstrated that the conditions work. Accordingly, the fact that methanol works as an inducer with some non-repressive substrates does not mean at all that formates (or formic acid) should work the same way. This is especially true as the mechanism of activation of the promoters is not yet clear. Consequently, no one can say with absolute certainty that a metabolite can be an inducer under certain growth conditions. While some regulatory transcription activation factors were elucidated for the intensively used AOX1 promoter, nothing is shown for all the other promoters of the MUT (Methanol UTilization) pathway examples of which are listed above (SEQ ID NOs:1-9).

According to an aspect of the invention, there is provided a method for producing a transgenic cell product comprising:

(a) providing an expression system comprising: a host cell comprising an expression vector, said expression vector comprising an inducible MUT (Methanol Utilization) pathway promoter operably linked to a nucleic acid molecule encoding a transgenic cell product of interest;

(b) growing the host cell on a suitable carbon source for supporting active growth of the host cell and for repressing the inducible MUT promoter, thereby providing a host cell culture;

(c) after the host cell culture has attained a suitable host cell culture density, growing the host cell culture on a non-repressing carbon source, thereby de-repressing the inducible MUT pathway promoter;

(d) adding an amount of an inducer compound selected from the group consisting of: formaldehyde; S-formylglutathione; S-hydroxymethyl glutathione; formic acid; an alkali metal or ammonium salt of formic acid; and an alkaline earth metal salt of formic acid; sufficient to induce the inducible MUT pathway promoter to the host cell culture such that the inducible MUT pathway promoter initiates expression of the nucleic acid molecule encoding the transgenic cell product of interest; and (e) recovering the expressed transgenic cell product of interest from the host cell culture.

According to another aspect of the invention, there is provided a method for producing a transgenic cell product comprising:

(a) providing an expression system comprising: a host cell comprising an expression vector, said expression vector comprising an inducible MUT (Methanol Utilization) pathway promoter operably linked to a nucleic acid molecule encoding a transgenic cell product of interest;

(b) growing the host cell on a suitable carbon source for supporting active growth of the host cell and for repressing the inducible MUT promoter, thereby providing a host cell culture;

(c) after the host cell culture has attained a suitable host cell culture density:

(c1) adding to the host cell culture a non-repressing carbon source, (c2) adding an amount of an inducer compound selected from the group consisting of: formaldehyde; S-formylglutathione; S-hydroxymethyl glutathione; formic acid; an alkali metal or ammonium salt of formic acid; and an alkaline earth metal salt of formic acid; sufficient to induce the inducible MUT pathway promoter to the host cell culture such that the inducible MUT pathway promoter initiates expression of the nucleic acid molecule encoding the transgenic cell product of interest; and (c3) recovering the expressed transgenic cell product of interest from the host cell culture; and (d) repeating steps (c1)-(c3).

DETAILED DESCRIPTION

Figure 1A:
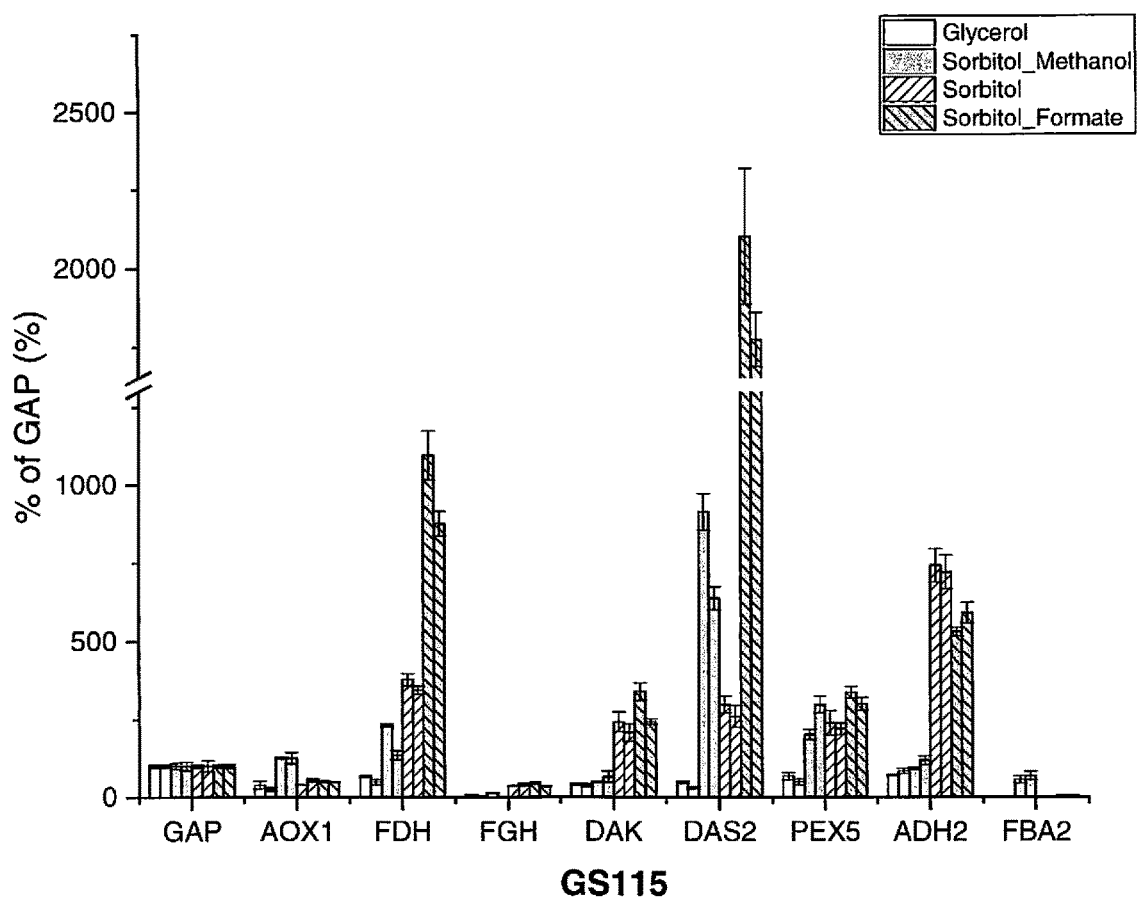
FIG. 1 Chart for promoters induction levels in response to glycerol, sorbitol, methanol and potassium formate. Double bars are for biological duplicates, error bars show standard deviation in RT-qPCR experiment; a) for GS115 strain; b) for KM71h strain FIG. 2 Schematic illustration integration of an expression cassette in yeast strain GS115 genome.

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell culture, molecular biology, immunology, microbiology, genetics, and protein and nucleic acid chemistry described herein is well-known and commonly used in the art. The methods and techniques provided herein are generally performed according to conventional methods well known in the art and as described in various general and more specific references that are cited and discussed throughout the present specification unless otherwise indicated. The nomenclatures used in connection with, and the laboratory procedures and techniques of molecular biology described herein are those well-known and commonly used in the art.

That the disclosure may be more readily understood, select terms are defined below.

The articles "a" and "an" are used herein to refer to one or to more than one (i.e., to at least one) of the grammatical object of the article. By way of example, "an element" means one element or more than one element.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "comprising" or "comprises" is intended to mean that the compositions and methods include the recited elements, but do not exclude others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than a trace amount of other ingredients and substantial method steps recited. Embodiments defined by each of these transition terms are within the scope of this invention.

The use of the term "or" in the claims is used to mean "and/or" unless explicitly indicated to refer to alternatives only, or the alternatives are mutually exclusive, although the disclosure supports a definition that refers to only alternatives and "and/or."

As used herein, the term "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The term "polynucleotide" refers to a double-stranded or single-stranded DNA, as well as complementary nucleic acid sequences. Polynucleotide includes a sequence of nucleoside or nucleotide monomers consisting of naturally occurring bases, sugars, and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine, and uracil. The sequences may also contain modified bases.

The term "protein" or "polypeptide" refers to a sequence of amino acid residues encoded by a nucleic acid molecule. Within the context of the present application, a polypeptide of the disclosure may in one embodiment include various structural forms of the primary protein. For example, a polypeptide of the disclosure may be in the form of acidic or basic salts or in neutral form. In addition, individual amino acid residues may be modified by oxidation or reduction. The proteins and polypeptides of the present disclosure may also include truncations, analogs, and homologs of the proteins and polypeptides as described herein having substantially the same function as the proteins or polypeptides of the present disclosure.

As used herein "construct" or "plasmid" refer to an artificially created nucleic acid, comprising a delivery vector and a gene(s) of interest, for example a vector comprising a polynucleotide described herein. The polynucleotide of interest can be cloned into a plasmid of interest to produce a construct. In an embodiment, the vector is an expression vector. Possible expression vectors include but are not limited to cosmids or plasmids, so long as the vector is compatible with the host cell used. The expression vectors are suitable for transformation of a host cell, which means that the expression vectors contain a polynucleotide such as those exemplified in the application and regulatory sequences selected on the basis of the host cells to confer the expression of a gene of interest.

Operatively linked (or operably linked) is intended to mean that the gene of interest is linked to regulatory sequences in a manner which allows expression of this gene of interest. In some embodiments, the isolated and/or purified nucleic acid molecules, polynucleotides or vectors, constructs, or in vitro expression systems comprising these isolated and/or purified nucleic acid molecules, may be used to create transgenic or recombinant organisms or recombinant cells (e.g. optionally cells of recombinant organisms) that produce polypeptides or any small molecule compound. A nucleotide sequence is associated in a manner of receiving, for example, a promoter is operably linked to a coding sequence of a recombinant gene when it can affect the expression of the coding sequence.

Described herein is an expression system for the production of for example recombinant proteins or small molecules, as discussed herein. In some embodiments, the expression system comprises a recombinant vector or a part thereof as disclosed herein. In some embodiments, the expression system comprises a suitable host cell, for example, a microbial cell, a yeast cell, a plant cell, or an animal cell. In another embodiment, the host expression system comprises a yeast cell. In one embodiment, the yeast cell comprises one or more of *Pichia pastoris, Komagataella kurtzmanii, Komagataella phaffii, Pichia angusta, Pichia guillermordii, Pichia methanolica, Pichia inositovera, Hansenula polymorpha, Candida boidinii*, and *Yarrowia lipolytica*.

As used herein "batch phase" refers to the first phase of culturing/fermentation upon inoculation where the culture grows to reach the needed optical density ($OD_{600}$) before induction phase. As discussed herein and as will be apparent to one of skill in the art, the specific $OD_{600}$ will depend on several factors, including but by no means limited to the transgenic cell product of interest, for example, a foreign peptide or small molecule, being produced; and the host cell being used.

As used herein "induction phase" or "fed-batch phase" or "continuous phase" refer to the second phase of culturing following the batch phase, where the culture is induced, which can be considered as switching on the expression of gene(s) of interest by adding a compound called an inducer.

According to an aspect of the invention, there is provided a method for producing a transgenic cell product comprising:

(a) providing an expression system comprising: a host cell comprising an expression vector, said expression vector comprising an inducible MUT (Methanol Utilization) pathway promoter operably linked to a nucleic acid molecule encoding a transgenic cell product of interest;

(b) growing the host cell on a suitable carbon source for supporting active growth of the host cell and for repressing the inducible MUT pathway promoter, thereby providing a host cell culture;

(c) after the host cell culture has attained a suitable host cell culture density, growing the host cell culture on a non-repressing carbon source, thereby de-repressing the inducible MUT pathway promoter;

(d) adding an amount of an inducer compound selected from the group consisting of: formaldehyde; S-formylglutathione; S-hydroxymethyl glutathione; formic acid; an alkali metal salt of formic acid; and an alkaline earth metal salt of formic acid; sufficient to induce the inducible MUT pathway promoter to the host cell culture such that the inducible MUT pathway promoter expresses the nucleic acid molecule encoding the transgenic cell product of interest; and (e) recovering the expressed transgenic cell product of interest from the host cell culture.

The inducible promoter may be selected from the group consisting of: NAD+-dependent formate dehydrogenase (FDH) promoter (one example of which is provided as SEQ ID NO:1); alcohol oxidase 2 (AOX2) promoter (one example of which is provided as SEQ ID NO:2); peroxin Pex14p (PEX14) promoter (one example of which is provided as SEQ ID NO:3); dihydroxyacetone kinase (DAK) promoter (one example of which is provided as SEQ ID NO:5); dihydroxyacetone synthase 1,2 (DAS1,2) promoter (examples of which are provided as SEQ ID NO:10 and SEQ ID NO:11 respectively); formyl-glutathione dehydrogenase (FGH) promoter (one example of which is provided as SEQ ID NO:4); formaldehyde dehydrogenase 1 (FLD1) promoter (one example of which is provided as SEQ ID NO:12); Fructose 1,6-bisphosphate aldolase (FBA) promoter (one example of which is provided as SEQ ID NO:6); Peroxisomal membrane signal receptor PTS1 (PEX5) promoter (one example of which is provided as SEQ ID NO:7); alcohol dehydrogenase 2 (ADH2) promoter (one example of which is provided as SEQ ID NO:8); and catalase (CAT) promoter (one example of which is provided as SEQ ID NO:9). As will be apparent to those of skill in the art, the promoter sequences provided in SEQ ID NOs: 1-12 are intended for illustrative purposes only and suitable variants of these may be used within the invention, depending on the host cell used.

The host cell may be a yeast cell, for example, selected from the group consisting of: *Pichia pastoris, Komagataella kurtzmanii, Komagataella phaffii, Pichia angusta, Pichia guillermordii, Pichia methanolica, Pichia inositovera, Hansenula polymorpha, Candida boidinii,* and *Yarrowia lipolytica*. In some embodiments, the yeast is *Pichia pastoris*.

In some embodiments, the nucleic acid molecule further comprises a secretion peptide in frame with the transgenic cell product of interest, preferably upstream in the direction of transcription and translation relative to the product of interest or gene of interest.

In some embodiments, the nucleic acid molecule further comprises an expression tag in frame with the transgenic cell product of interest, preferably at the C-terminus or N-terminus of the product of interest or gene of interest.

The suitable host cell culture density may be 250-350 g/L of culture (wet cell weight).

As discussed herein, in some embodiments of the invention, steps (c), (d) and (e) are repeated more than once. Specifically, especially when the transgenic cell product of interest includes a secretion sequence, the transgenic cell product of interest may be recovered from the growth media and additional non-repressing carbon source and inducer compound may be added to sustain growth of the host cell culture in batch phase so that product continue to be produced by the cells and recovered from the media.

In some embodiments, the host cell culture density is determined prior to adding the induction compound so that the inducer compound is added at a concentration that is sufficient to induce the inducible promoter at that host cell culture density.

In some embodiments, the non-repressing carbon source is initially added to the host cell culture in stages, for example, starting prior to exhaustion of the growth repressing carbon source so that initially the host cell culture is growing on both the repressing carbon source and the non-repressing carbon source. In some embodiments, the repressing carbon source is the major carbon source initially and the levels thereof are allowed to decrease until the non-repressing carbon source is the sole carbon source. As discussed herein, this prevents lags in growth of the host cell culture, as there is a gradual transition from the repressing carbon source to the non-repressing carbon source rather than an abrupt shift.

The non-repressing carbon source may be selected from the group consisting of sorbitol, mannitol, trehalose and alanine.

The fermentable repressing carbon source may be glycerol or glucose.

In some embodiments, the expression vector or recombinant vector comprises an origin of replication that enables the vector to propagate in, for example, *E. coli* for amplification and cloning purposes.

In some embodiments, the recombinant vector comprises selectable "marker genes", which enable the selection of host cells (both *E. coli* and yeast cells) transformed with a recombinant cassette of the application. Examples of selectable marker genes include but are by no means limited to genes encoding for proteins such as aminoglycoside 3'-phosphotransferase which confers resistance to G418 antibiotic, or hygromycin B phosphotransferase which confers resistance to hygromycin. Other suitable selectable marker genes will be readily apparent to one of skill in the art.

In some embodiments of the invention, the expression vector further comprises a secretion peptide (e.g. αMF) that is for example linked or fused or in frame with the transgenic cell product of interest so that when expression of the transgenic cell product of interest is driven by the inducible promoter, the peptide or polypeptide that is produced from the resulting transcript includes a secretion peptide which directs the nascent polypeptide chain to the secretion pathway, as discussed herein. In this manner, the product of the gene of interest (GOI) is operably linked downstream of the secretion peptide.

In some embodiments, the polypeptide produced by the expression vector further comprises, at the C' or N' terminal thereof, a detection tag that facilitates the detection of the protein of interest for example by means of Western Blotting. As will be known by those of skill in the art, human influenza hemagglutinin (HA) tag, Myc tag, FLAG tag or HIS tag are examples of short peptides that can be used as a detection tag.

As discussed herein, the repressing carbon source may be any fermentable carbon source, for example, but by no means limited to glycerol or glucose.

As will be apparent to those of skill in the art, as used herein, "batch phase" indicates intensive culture growth, for example, so that the host cell culture reaches high densities, e.g. 250-350 g/L of culture (wet cell weight).

As will be appreciated by one of skill in the art and as discussed herein, the specific density of the host cell culture when the carbon source is switched from a repressive carbon source to a non-repressive carbon source may vary, depending on the product being expressed and the desired outcome. As such, while a lower cell density will in theory produce less protein, this may be desirable if the product or protein being produced is for example toxic to the cell or otherwise problematic to synthesize and/or recover at higher densities. Similarly, while higher cell densities may not be healthy for the culture overall, in some embodiments, this higher density may be desirable for efficient production of the product.

As discussed herein, while not wishing to be bound to a particular theory or hypothesis, it is believed that the inducer compound is degraded by formate dehydrogenase.

As discussed herein, the inducer compound may be added and the transgenic cell product of interest recovered from the host cell culture multiple times, depending of course on the nature of the transgenic cell product being produced. As will be apparent to one of skill in the art, in these embodiments, it may be desirable to incorporate a secretion peptide into the nucleic acid molecule encoding the transgenic cell product to facilitate recovery and permit multiple "induction and recovery" stages. In these embodiments, non-repressing carbon source may also be fed, either continuously or in batches, to the host cell culture, as discussed herein.

The disclosure provides a method for producing added value products like polypeptides or small molecule compounds by the culturing of methylotrophic yeast without use of methanol as an inducer, that is, with the proviso that no methanol is added as an inducer. Instead, the method uses a non-repressing carbon source for feeding and an alternative inducer for expression of (a) gene(s) of interest. Accordingly, in one embodiment, provided herein is a process for producing added value compounds using methylotrophic yeast host expression system that comprises (a) nucleotide sequence(s) encoding the gene(s) of interest, comprising (i) culturing the yeast host cells in a batch phase providing a feeding for robust growth; and (ii) culturing the host expression system in a fed-batch phase providing a feeding with an alternative inducer, or (ii) culturing the host expression system in a continuous phase providing feeding in continuous fermentation regime with an alternative inducer.

The batch and fed-batch phases carbon source, can be any carbon source except methanol. In one embodiment, the first and/or the second sources comprise one or more of glycerol, alanine, lactate, glycerol, glucose, ethanol, citrate, sorbitol, xylose, trehalose, arabinose, fructose, melibiose, maltose, rhamnose, mannose, mannitol, and raffinose. In one embodiment, the batch phase carbon source is glycerol. In another embodiment, the fed-batch and induction phase carbon source is sorbitol. Among them glucose, glycerol, ethanol, citrate, xylose, arabinose, fructose, melibiose, maltose, rhamnose, mannose, and raffinose belong to repressing carbon sources; whereas sorbitol, mannitol, alanine and trehalose are non-repressing carbon sources.

The continuous and induction phase carbon source can be any non-repressing carbon source except methanol. In one embodiment, the first and/or the second sources comprise one or more of alanine, sorbitol, mannitol. In one embodiment, the induction phase carbon source is sorbitol.

In one embodiment, a promoter is a regulatory nucleotide sequence that drives expression of a gene of interest.

In one embodiment, an inducer is a compound that regulates gene expression.

In one embodiment, an inducer comprises one or more of formaldehyde, S-formylglutathione, S-hydroxymethyl glutathione, formic acid or any alkali metal or ammonium salt of formic acid or an alkaline earth metal salt of formic acid is used. Exemplary of such inducers are sodium formate, potassium formate, and ammonium formate.

In one embodiment, the regulatory sequence is a promoter. The promoter is a regulatory nucleotide sequence in the host cell or host expression system that drives the expression of a gene of interest. In another embodiment, the promoter is a constitutive promoter or an inducible promoter. In one embodiment, the promoter is selected from a group consisting of, the FDH promoter ($NAD^+$-dependent formate dehydrogenase) promoter, the Alcohol oxidase 2 (AOX2) promoter, a dihydroxyacetone kinase (DAK) promoter, a Dihydroxyacetone synthase 1,2 (DAS1,2) promoter, the Formyl-glutathione dehydrogenase (FGH) promoter, the Formaldehyde dehydrogenase 1 (FLD1) promoter, the Fructose 1,6-bisphosphate aldolase (FBA) promoter, the Peroxisomal membrane signal receptor PTS1 (PEX5) promoter, the Alcohol dehydrogenase 2 (ADH2) promoter, and a Catalase (CAT) promoter.

In one embodiment, the media comprising the host expression system is oxygenated. In another embodiment, the batch phase feed is provided at a rate that maintains a specific growth rate ($\mu$) of the host expression system in the culture to be in a range from about $0.03\ h^{-1}$ to about $0.5\ h^{-1}$. In another embodiment, the fed-batch phase or continuous feed is provided at a rate that maintains a specific growth rate (p) of the host expression system in the culture to be in a range from about $0.0001\ h^{-1}$ to about $0.465\ h^{-1}$.

For illustrative purposes, it is of note that a very fast specific growth rate for the host cell, for example, growth during the batch phase, is considered to be about $0.3$-$0.4\ h^{-1}$, whereas a slow specific growth rate may be for example about $0.01$-$0.04\ h^{-1}$, which may be the growth rate of the cells during the induction phase. As will be appreciated by one of skill in the art, in some embodiments, the non-repressing carbon source is supplied to or present in the growth medium at a concentration or percentage that will support growth of the host cell culture at about $0.3$-$0.4\ h^{-1}$ while the non-repressing carbon source is supplied to or present in the growth medium at a concentration or percentage that will support growth of the host cell culture at about $0.01$-$0.04\ h^{-1}$.

In some embodiments, the batch phase and fed-batch/continuous phase are each carried out at a temperature of about 21° C. to about 30° C. In one embodiment, the batch phase and fed-batch phase are each carried out at a temperature of about 25° C.

In one embodiment, the polypeptide is a heterologous polypeptide.

In some embodiments, the polypeptide comprises about ten or more amino acids.

The term "heterologous" refers to a polynucleotide, gene, polypeptide, or an enzyme not normally found in the host organism (e.g., recombinant cell). "Heterologous" also includes a native coding region, or portion thereof, that is reintroduced into the host organism in a form that is different from the corresponding native gene, e.g., not in its natural location in the host's genome. The heterologous polynucleotide or gene may be introduced into the host organism by, e.g., gene transfer, for example, by transformation or transfection. A heterologous gene may include a native coding region that is a portion of a chimeric gene including non-native regulatory regions that is reintroduced into the native host. Foreign genes can be conceptualized as native genes inserted into a non-native organism, or chimeric genes. Thus, "heterologous" polypeptides are those polypeptides foreign to the host cell being utilized, such as a plant or human protein being produced by yeast or bacteria. While the heterologous polypeptide may be prokaryotic or eukaryotic, in some embodiments it is eukaryotic. In some embodiments, it is a plant or human protein or peptide. In some embodiments, it is a polypeptide (e.g., enzyme).

Variants and/or fragments of the polypeptides described herein may also be prepared by the methods disclosed herein.

In some embodiments, activity of a polypeptide of the present invention, including activity of the variants and fragments thereof, can be determined by methods known in the art.

In one embodiment, the polypeptide is human epidermal growth factor (hEGF) comprising the amino acid sequence set forth in SEQ ID NO:17 (NCBI Accession No. XP_016863338.1) hEGF) is a ~6.2 kDa polypeptide composed of 53 amino acid residues with three intramolecular disulfide bonds. One of its major biological functions is to promote the generation of new epithelial and endothelial cells, and to stimulate tissue repairs. hEGF had been produced in various host systems including *Escherichia coli*, *Saccharomyces cerevisiae* and baculovirus. In *E. coli*, the produced hEGF tends to form inclusion bodies, which dramatically complicates downstream processes, because it requires laborious procedures of refolding and multistep purification.

In another embodiment, the polypeptide is an extracellular superoxide dismutase [Cu—Zn](hSOD3) comprising the amino acid sequence set forth in SEQ ID NO:18 (NCBI Accession No. NP_003093.2) SOD is a ~30 kDa polypeptide and reported to be a multimeric glycoprotein composed of at least four identical subunits in human extracellular fluids with heterogeneous affinity for heparin. The potential demand for SOD in human healthcare is growing up; therefore, production of biological active SOD is of a great interest. Production of therapeutic proteins by genetically engineered yeasts was shown to be a cost-effective alternative to tissue cultures or purification from animal tissues.

In another embodiment, the polypeptide is a human Lactoferrin (hLF) comprising the amino acid sequence set forth in SEQ ID NO:19 (NCBI Accession No. AAB60324.1) Lactoferrin (LF) is a member of the transferrin family of iron-binding glycoproteins. It was originally found in mammalian exocrine secretions and in specific granules of polymorphonuclear leukocytes.

In another embodiment, the polypeptide is the receptor binding domain (RBD) of S (spike) glycoprotein of SARS-CoV-2 virus comprising the amino acid sequence set forth in SEQ ID NO:20 (PDB: 7CM4_A). The surface exposed location of the S glycoprotein renders it a direct target for host immune responses, making it the major target of neutralizing antibodies. The S protein is considered to be a primary target for vaccine design as well as antiviral therapeutics.

A polypeptide prepared by the method of the present invention can be isolated after expression by techniques known in the art, including, but not limited to, affinity chromatography, ion-exchange chromatography, antibody affinity, size-exclusion, or any other method that eliminates a substantial portion of the culture and/or cellular debris from the polypeptide. In some embodiments, the process provides a substantially purified polypeptide. The isolated polypeptide can have activity similar to the corresponding native protein that it is derived from. The polypeptide can be isolated in a correctly folded state or conformation, approximating that of the native protein, or can be further renatured or modified to put it into a correctly folded conformation using a variety of methods and/or reagents known in the art.

In one embodiment, the host cells are *Pichia pastoris* (e.g., *Komagataella* spp), *Pichia angusta*, *Pichia guillermordii*, *Pichia methanolica*, or *Pichia inositovera*.

In some embodiments, the recombinant or host cell is *Pichia pastoris*.

In other embodiments, the recombinant or host cell is a Mut$^S$(methanol utilization slow) strain of *P. pastoris* KM71 and KM71h. It is of note however that Mut$^+$ strains such as GS115 may be used within the invention and use of a Mut$^s$ strain is not a requirement of the invention.

In another embodiment, the host cell or recombinant cell is *Hansenula polymorpha*, *Candida boidinii*, or *Yarrowia lipolytica*.

In one embodiment, a heterologous polynucleotide encoding the polypeptide is provided on a vector (e.g., plasmid) suitable for integration into the genome of the host cell in single or multiple copies per host cell. In some embodiments, the vector is a nucleotide sequence integrated into the genome.

In one embodiment, the vector is a eukaryotic expression vector, preferably a yeast expression vector.

In another embodiment, the expression vector is a cloned recombinant nucleotide sequence, such as the DNA sequence required for transcription of one or more recombinant gene(s) or peptides of interest and their mRNA translation in appropriate host organisms.

In other embodiments, such expression vectors typically include one or more of an origin for autologous replication in a host cell, an appropriate marker (e.g., gene that confers resistance to antibiotics such as zeocin, kanamycin G418 or hygromycin), a restriction enzyme cleavage site, an appropriate promoter sequence and a transcription terminator, and these components are operably linked to interact with each other.

In some embodiments, expression vectors include, but are not limited to, cloning vectors, modified cloning vectors, and specifically designated plasmids. The expression vector of the present invention may be any expression vector suitable for expression of a recombinant gene in a host cell, which is selected according to the host organism.

In other embodiments, regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In some embodiments, the nucleotide sequence of the gene of interest is under the control of a constitutive promoter, a promoter responsive to a carbon source which is fed during a batch phase of culturing, and/or a promoter responsive to a carbon source and to an inducer, which is fed/added during a fed-batch phase of culturing In one embodiment, the promoter is an endogenous promoter, wherein the polynucleotide encoding the polypeptide is integrated into the genome of the yeast host cell such that the endogenous promoter is operably linked to the heterologous polynucleotide, thereby capable of driving its expression.

In other embodiments, the expression vector pL (SEQ ID NO:3) further comprises a secretory leader sequence effective for inducing the secretion of polypeptide from the host cell.

In other embodiments, the expression vector pL (SEQ ID NO:13) further comprises the HA-tag (Hemagglutinin tag) for the routine detection by Western Blot using anti-HA-tag antibodies.

In some embodiments, the secretory leader sequence may originate from a yeast α-factor source, for example from αMF, yeast phosphatase (PHO), heat shock proteins (HSP), as well as HSP tag repeats, invertase (SUC2) tag, OST1 tag, DDDK tag or combination thereof, or any other secretion peptide described in the literature.

In some embodiments, the step of growing the recombinant cell comprising the heterologous polynucleotide includes growing the cell in a medium comprising a first carbon source, for example, a fermentable or repressing carbon source.

Examples of other ingredients that may be added to the medium are discussed herein; however, suitable ingredients and the amounts thereof will be readily apparent to those of skill in the art and/or may be determined through routine experimentation.

In one embodiment, the medium is an aqueous medium comprising the first carbon source, and optionally one or more further ingredients such as, for example, salts (e.g., phosphate and/or sulphate, and the like), antibiotics, vitamins, trace metal ions, agents to keep the pH at a desired level, phosphate salts, and/or antifoaming agents.

In another embodiment, the medium comprises one or more of phosphoric acid, calcium sulfate, potassium sulfate, magnesium sulfate, potassium hydroxide, and glycerol.

In some embodiments, the medium further comprises one or more of cupric sulfate, sodium iodide, manganese sulfate, sodium molybdate, boric acid, cobalt chloride, zinc chloride, ferrous sulfate, biotin, and sulfuric acid.

In other embodiments, the batch and fed-batch carbon source (or first carbon source) comprises one or more of alanine, lactate, glycerol, glucose, ethanol, citrate, sorbitol, xylose, trehalose, arabinose, fructose, melibiose, maltose, rhamnose, mannose, mannitol, and raffinose.

In one embodiment, the continuous and induction phases carbon source (or second carbon source or non-repressing carbon source) comprises one or more of alanine, sorbitol, mannitol, and trehalose.

Specifically, whereas the conventional yeast (S. cerevisiae) prefers glucose or its precursors (disaccharides) so that to assimilate it through glycolysis, methylotrophic yeast like Pichia pastoris prefer glycerol as a carbon source assimilating it through G3P (glycerol-3-phosphate)—DHAP (dihydroxyacetone phosphate) pathway. However, Pichia cultures can readily use glucose as well. Considering that glycerol is cheaper, most culturing processes are designed for glycerol use in batch phase In some embodiments, the batch phase and/or the fed-batch carbon source are non-fermentable carbon sources.

For example, in one embodiment, in a batch phase, the recombinant cell is cultured in a saline medium with a glycerol.

For example, is some embodiments, the recombinant cell comprising the heterologous polynucleotide is grown in the medium in a fermenter, which, as used herein, also refers to for example a bioreactor or any other suitable apparatus for culturing the recombinant cells) employing a batch protocol whereby the cells are grown using the first carbon source (e.g., glycerol). Cell growth may be monitored periodically and may continue until the first carbon source (e.g., glycerol) is consumed. In some embodiments, complete consumption of the first carbon source (e.g., glycerol) is indicated by a spike in dissolved oxygen (DO) levels to 100%. The length of time needed to consume all the first carbon source (e.g., glycerol) can vary depending on the density of the initial inoculum. That is, addition glycerol or other fermentable carbon source may be added in order to bring the host cell culture density to the desired density.

In some embodiments, sampling of the culture to measure cell density may be performed at the end of the first carbon source (e.g., glycerol) feed stage, e.g., cell density can be measured by withdrawing a sample from e.g., the fermenter at each timepoint and using an aliquot for measuring cell density e.g., at a wavelength of 600 nm. In other embodiments, cell growth can be evaluated by measuring the wet cell weight, pH, microscopic purity, protein concentrations and/or activity.

In some embodiments, the step of growing comprises adding a culture comprising the cell to the medium comprising the first carbon source.

In another embodiment, an initial amount of the first carbon source in the medium is at about 4% by volume of the first carbon source.

In other embodiments, after consumption of glycerol (e.g., at completion of the batch phase), a carbon source-limited (e.g., glycerol-limited) feeding phase (e.g., employing a fed-batch protocol) follows e.g., until the desired level of biomass is reached. In other embodiments, after consumption of glycerol (e.g., at completion of the batch phase), a glycerol-limited feeding phase commences until a desired level of the biomass is reached.

Thus, in some embodiments, once the first-carbon source (e.g., glycerol) is depleted during the batch phase (e.g., glycerol batch phase), a second phase (e.g., glycerol fed-batch phase) is begun by adding the appropriate carbon source (e.g., glycerol) to the medium at a limiting growth rate of the recombinant cells.

For example, in one embodiment, the step of growing further comprises continuously adding the first carbon source to the medium at a first feed rate from a solution comprising the first carbon source.

In another embodiment, the feed rate of the fed-batch carbon source is provided at such a rate so to maintain the specific growth rate (p) of the culture in the range 0.001-0.5 $h^{-1}$.

In another embodiment, the first feed rate is initiated after the initial amount of the batch phase carbon source is completely consumed by the culture.

In other embodiments, the step of culturing comprises adding the fed-batch carbon source to the medium at a second feed rate and decreasing the first feed rate. As discussed herein, this provides a gradual transition from growth of the host cell culture on the repressing carbon source to growth on the non-repressing carbon source.

In another embodiment, the feed rate of the continuous and/or induction phase carbon source is provided at such a rate so to maintain the specific growth rate (p) of the culture in the range 0,001-0,5 $h^{-1}$.

In other embodiments, once the transition from the first carbon source feed to the second carbon source feed is completed, an aqueous solution comprising the second carbon source and trace salts is introduced into the medium.

In one embodiment, the second carbon source (e.g., sorbitol) feed is stopped if DO cannot be maintained above 20%, then resumed when the DO increases to at least about 20%. For example, increasing agitation, aeration, pressure and/or oxygen feeding can help increase and/or maintain the DO above 20%. Generally, culturing of methylotrophic yeast is carried out under aerobic conditions, so the cells are respiratory active on either of the substrates. Gradual increase of DO means that the culture has not adapted to the new carbon source yet and not actively consuming it. So, adding more of the second carbon source when DO is not stabilized yet and still is in uptrend can lead to accumulation of the substrate to a stressful threshold concentration. As will be appreciated by one of skill in the art, the repressing carbon source used in batch and fed-batch phases needs to be completely depleted for efficient inducing of the listed promoters to be obtained upon adding an inducing agent.

In one embodiment, the inducer comprises one or more of formaldehyde, S-formylglutathione, S-hydroxymethyl glutathione, formic acid or any alkali metal salt of formic acid or an alkaline earth metal salt of formic acid.

In another embodiment, the inducer comprises sodium formate, potassium formate, and/or ammonium formate.

In some embodiments an inducer is added by doses or boluses in amount of 0.001-2.0 g per 1 L of the culture up to 20 times a day.

While not wishing to be bound to a particular theory or hypothesis, when the formates or formic acid is added, it is apparently degraded by $NAD^+$ dependent formate dehydrogenase enzyme (FDH) produced by Pichia pastoris cells, so it is depleted in a while. It is not well known how fast it is dissimilated but there is an increase in yield in some cases when it is added it up to 3-4 times a day.

For example, in one embodiment, during the induction phase the 50% (w/v) solution of potassium formate is added in amount of 1 g/1 L of the culture 2 times a day.

In one embodiment, the method of the present invention allows the production of a heterologous polypeptide or any other added value compound without methanol or with the proviso that no methanol or substantially no methanol, that is, insufficient methanol on its own, is added.

In other aspects, the present invention provides a method for producing recombinant proteins and other added value compounds without use of methanol as an inducer. Instead, the method uses a sorbitol feeding and/or an alternative induction strategy for induction gene(s) of interest.

In some embodiments, the first and/or the second carbon sources can be any carbon source except methanol. In one embodiment, the first and/or the second sources comprise a compound selected from the group consisting of alanine, lactate, glycerol, glucose, ethanol, citrate, sorbitol, xylose, trehalose, arabinose, fructose, melibiose, maltose, rhamnose, mannose and raffinose. In one embodiment, the batch and fed-batch phases carbon source is glycerol and the induction phase carbon source is sorbitol.

The invention will be further described in the following examples, which do not limit the scope of the invention described in the claims.

EXAMPLES

Example 1

Assessment the Induction Potential or Strength of the Set of Promoters from Pichia pastoris (Komagataella phaffii) Strains KM71h and GS115.

The induction pattern of the following promoters were assessed by the measuring the transcription level by means RT-qPCR method: FDH promoter ($NAD^+$-dependent formate dehydrogenase) promoter, the Alcohol oxidase 1 (AOX1) promoter, the dihydroxyacetone kinase (DAK) promoter, the dihydroxyacetone synthase 2 (DAS2) promoter, the Formyl-glutathione dehydrogenase (FGH) promoter, the Fructose 1,6-bisphosphate aldolase (FBA) promoter, the Peroxisomal membrane signal receptor PTS1 (PEX5) promoter, the Alcohol dehydrogenase 2 (ADH2) promoter. Constitutive GAP (Glyceraldehydes-3-phosphate dehydrogenase) promoter's induction level was used as a reference.

The yeast cultures Pichia pastoris GS115 and KM71h strains were grown under repressed, derepressed and induced conditions. The repressed conditions suggest a repressive carbon source in a media, which makes the involved promoters repressed, for example glycerol. The derepressed conditions suggest a non-repressive carbon source in the media, for example sorbitol or any depleted carbon source, which switches the involved promoter to derepressed state. Induced conditions suggest the addition of a compound inti the media, called an inducer, which makes the involved promoters induced.

The culture of P. pastoris strain GS115 was inoculated from YPD plate into the shacking flask with 10 ml of liquid YPD. The culture was growth overnight and reinoculated in a following way:

1% of inoculum to three flasks with 10 ml of YN media (+histidine)+1% (v/v) glycerol, which represents repressed conditions 1% of inoculum to three flasks with 10 ml of YN media (+histidine)+1% (w/v) D(+) sorbitol, which represents derepressed conditions 1% of inoculum to three flasks with 10 ml of YN media (+histidine)+1% (w/v) D(+) sorbitol+0.2% (v/v) methanol, which represents induced conditions 1% of inoculum to three flasks with 10 ml of YN media (+histidine)+1% (w/v) D(+) sorbitol+1% (w/v) potassium formate, which represents induced conditions Those 4 media represent repressed, derepressed and induced (both with methanol and formate) conditions. The cultures were incubated in a temperature-controlled orbital shaker at 29° C., 250RPM for 6 hours followed by harvesting the biomass. Total RNA was extracted with RNeasy kit (Qiagen, Germany) according to the manufacturer's protocol. Reverse transcription was done with the High-Capacity cDNA Reverse Transcription Kit (ThermoFisher Scientific, USA). Specific primers for each appropriate gene: FDH, FGH, DAK, DAS2, AOX1, FBA, PEX5 and ADH2 were used for RT-PCR to assess the level of their transcription and thus the induction level of the respective promoter. The SYBR green method was used for RT-PCR, with the SYBR® Green qPCR master mix (Bio-Rad, USA) according to the manufacturer's protocol. The experiment was carried out in biological duplicates. Error bars in the FIG. 1 show the standard deviation in RT-qPCR method.

The ΔCt method was used for building standard curves. GAP gene (D-glyceraldehyde 3'-phosphate dehydrogenase) was used as a standard reference gene.

List of the primers used for RT-PCR qGAP_for; CTGGTGTCGACTACGTCATTGAGTC (SEQ ID NO:22)
qGAP_rev; GCATTGGAGACAATGTTCAAGTCAG (SEQ ID NO:23)
qFDH_for; ACTCCATTCCATCCAGCCTACATC (SEQ ID NO:24)
qFDH_rev; CATAACGACATGCTCAGCCACTG (SEQ ID NO:25)
qFGH_for; CTTCAACACAAGTCCGATGAGACG (SEQ ID NO:26)
qFGH_rev; GGTTGCCAAAATGCCTTCTCTG (SEQ ID NO:27)
qDAS2_for; GGCCAAGTACGGTTTCGATGTC (SEQ ID NO:28)
qDAS2_rev; CCTCTAATACGGGCCTTTAATTCCTCA (SEQ ID NO:29)
qDAK_for; AGGACACGAGCCTCTACATGCTG (SEQ ID NO:30)
qDAK_rev; GGCAAGACCGAAGTGAAGAATGTC (SEQ ID NO:31)
qAOX1_for; GTGAGCACACTGAGACCACATGG (SEQ ID NO:32)
qAOX1_rev; GAGCGGTGGTGTAGGTGTTACAAC (SEQ ID NO:33)
qFBA2_for; AAAAGCGGTGTCATCGTTGGAG (SEQ ID NO:34)
qFBA2_rev; TGGAAAAAAGCAGCACCTCCC (SEQ ID NO:35)
qPEX5_for; ACACAACATGACACATCCTTGCAAC (SEQ ID NO:36)
qPEX5_rev; TGCATTACGTTCAGCTCGTGTTG (SEQ ID NO:37)
qADH2_for; AAGGGTGACTGGCCATTGGAC (SEQ ID NO:38)
qADH2_rev; TTGGCACAACTGGATTCAGCAC (SEQ ID NO:39)

Figure 1B:
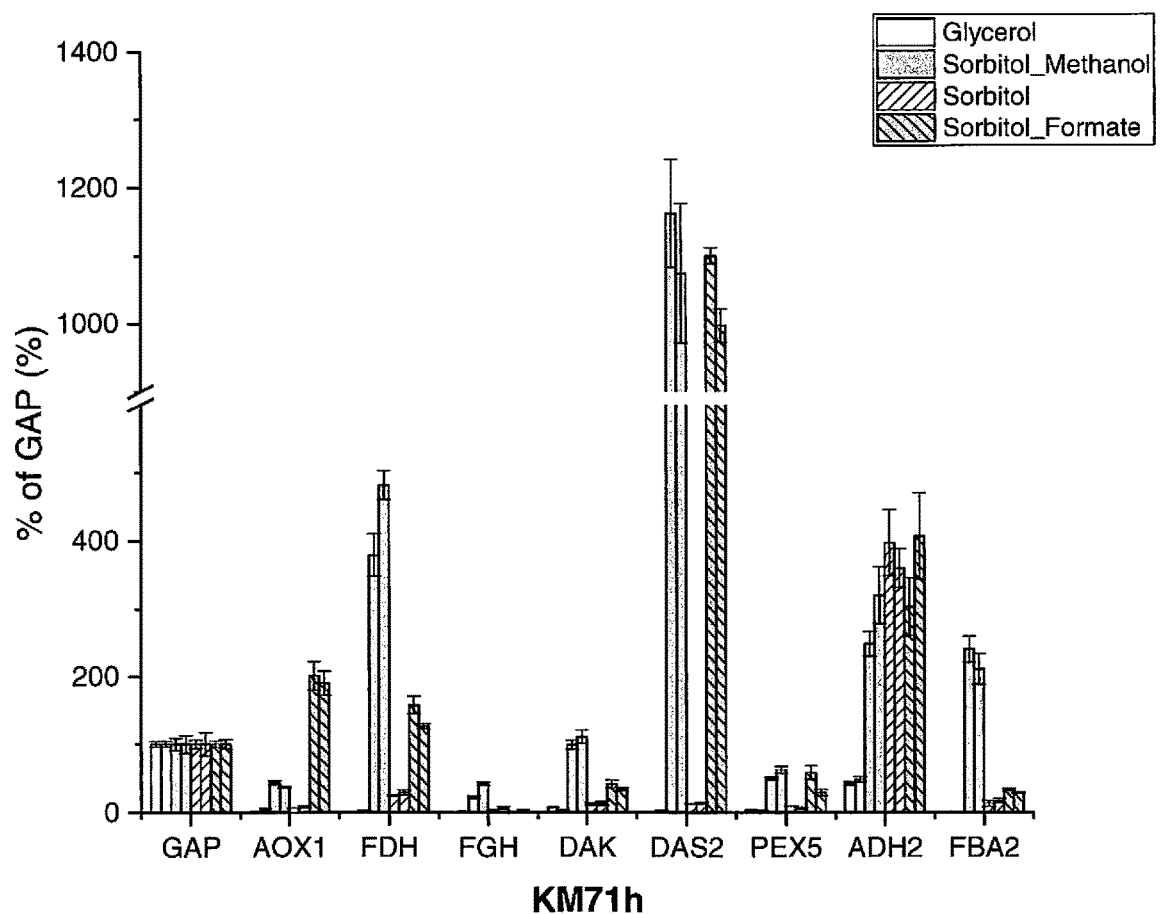

The results are shown in the FIG. 1

YN medium (+histidine): 6.7 g of Yeast Nitrogen Base with Ammonium sulphate; 20 mg L-histidine; bring to 1 l with distilled water.

Example 2

Figure 2:
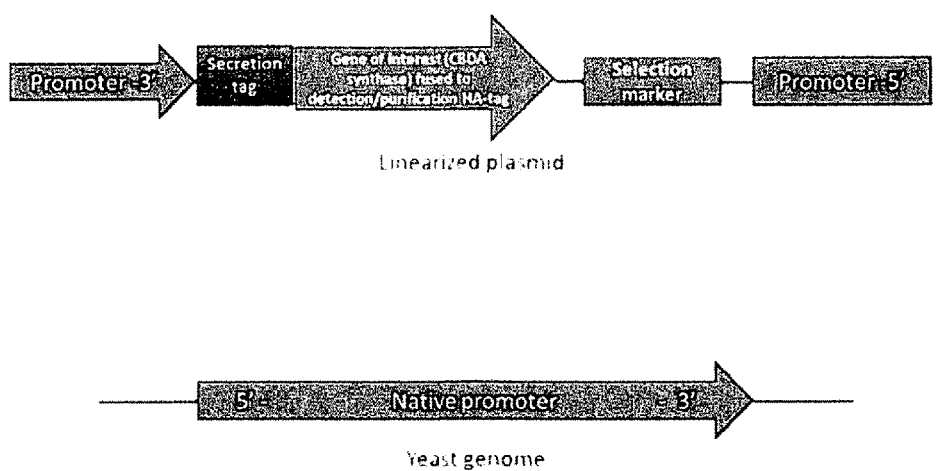
Figure 3:
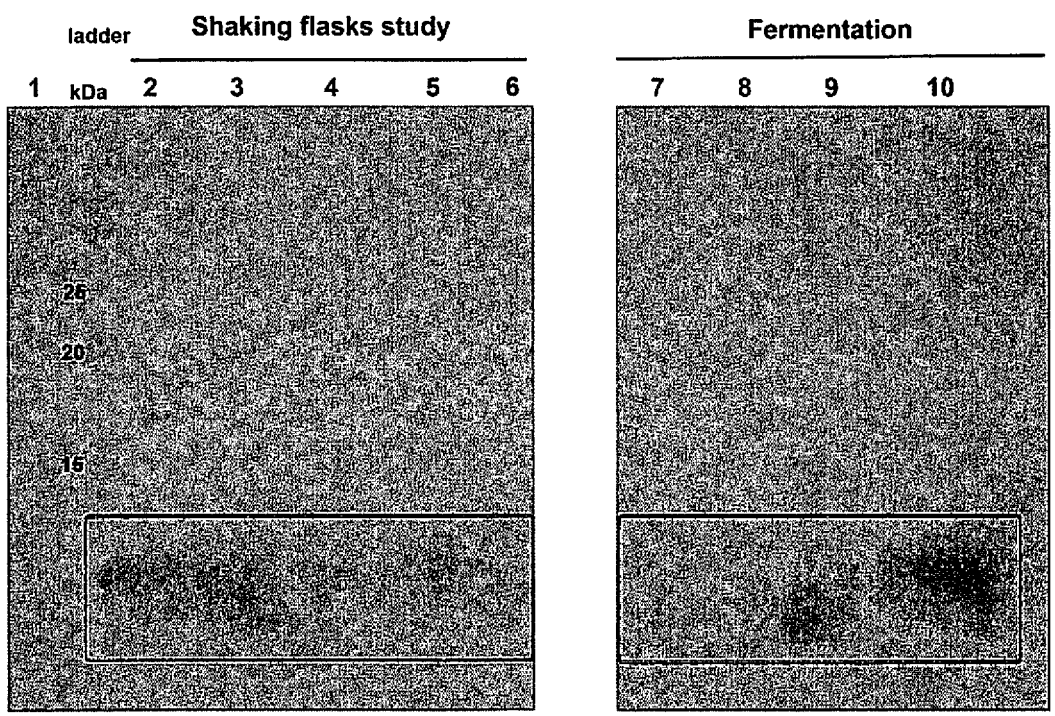
FIG. 3 Western blot of the samples from shaking flasks experiments and fermentation of GS115/pL_hEGF; The bands for EGF are shown in a frame 1. GS115 (negative control); protein ladder (catalog no. BZ0011G, BioBasic, Canada); 2. GS115/pL_hEGF clone #1 methanol induced culture; 3-6. GS115/pL_hEGF clones #1-4 potassium formate induction; 7. GS115/pL_hEGF fermentation samples with methanol induction/48 hours of culturing; 8. GS115/pL_hEGF fermentation samples with methanol induction/72 hours of culturing; 9. GS115/pL_hEGF fermentation samples with potassium formate induction/48 hours of culturing; 10. GS115/pL_hEGF fermentation samples with potassium formate induction/72 hours of culturing FIG. 4 Western blot of the samples from shaking flasks experiments and fermentation of GS115/pL_hSOD3; The bands for SOD3 are shown in a frame 1. GS115 (negative control); protein ladder (catalog no. BZ0011G, BioBasic, Canada); 2. GS115/pL_hSOD3 methanol induced culture; 3. GS115/pL_hSOD3 potassium formate induction; 4. GS115/pL_hSOD3 fermentation samples with methanol induction/48 hours of culturing; 5. GS115/pL_hSOD3 fermentation samples with methanol induction/72 hours of culturing; 6. GS115/pL_hSOD3 fermentation samples with potassium formate induction/48 hours of culturing; 7. GS115/pL_hSOD3 fermentation samples with potassium formate induction/72 hours of culturing FIG. 5 Western blot of the samples from shaking flasks experiments and fermentation of GS115/pL_hLF; The bands for LF are shown in a frame 1. GS115 (negative control); protein ladder (catalog no. BZ0011G, BioBasic, Canada); 2. GS115/pL_hLF clone #1 methanol induced culture; 3-6. GS115/pL_hLF clones #1-4 potassium formate induction; 7. GS115/pL_hLF fermentation samples with methanol induction/24 hours of culturing; 8. GS115/pL_hLF fermentation samples with methanol induction/48 hours of culturing; 9. GS115/pL_hLF fermentation samples with methanol induction/72 hours of culturing; 10. GS115/pL_hLF fermentation samples with potassium formate induction/24 hours of culturing; 11. GS115/pL_hLF fermentation samples with potassium formate induction/48 hours of culturing; 12. GS115/pL_hLF fermentation samples with potassium formate induction/72 hours of culturing FIG. 6 A. SDS-PAGE of the sample from shaking flasks experiment. Protein ladder (catalog no. BZ0011G, BioBasic, Canada); GS115/pL_RBD potassium formate induction; B. Western blot of the sample from shaking flasks experiment. Protein ladder (catalog no. BZ0011G, BioBasic, Canada); GS115/pL_RBD potassium formate induction; The bands for RBD are shown in frame.
Figure 4:
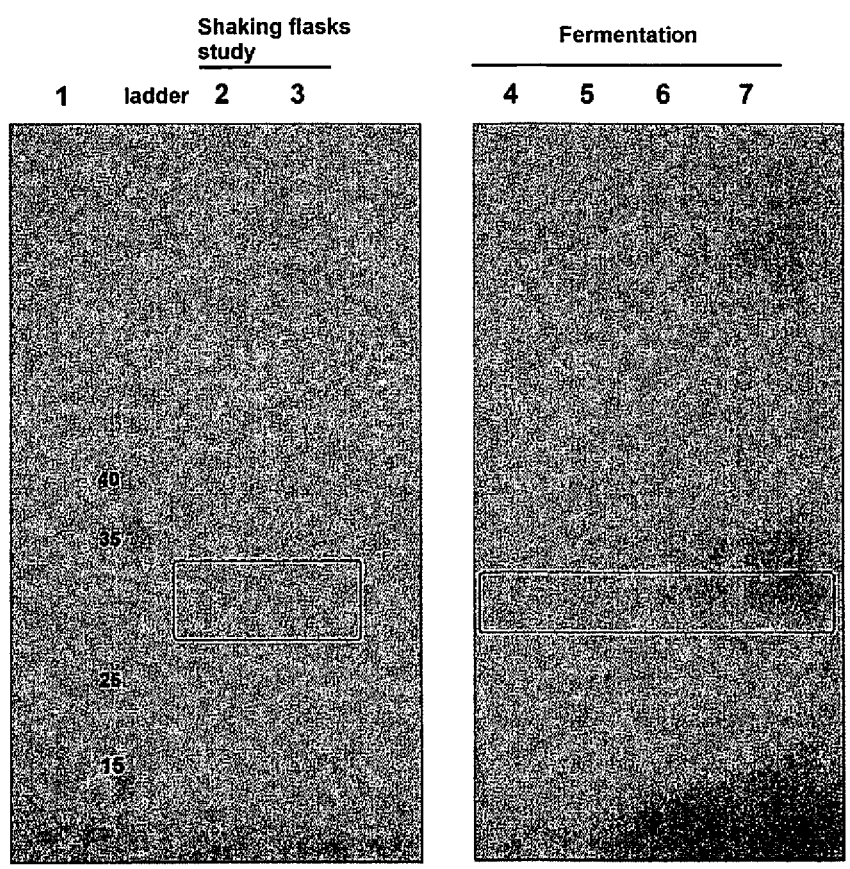
Figure 5:
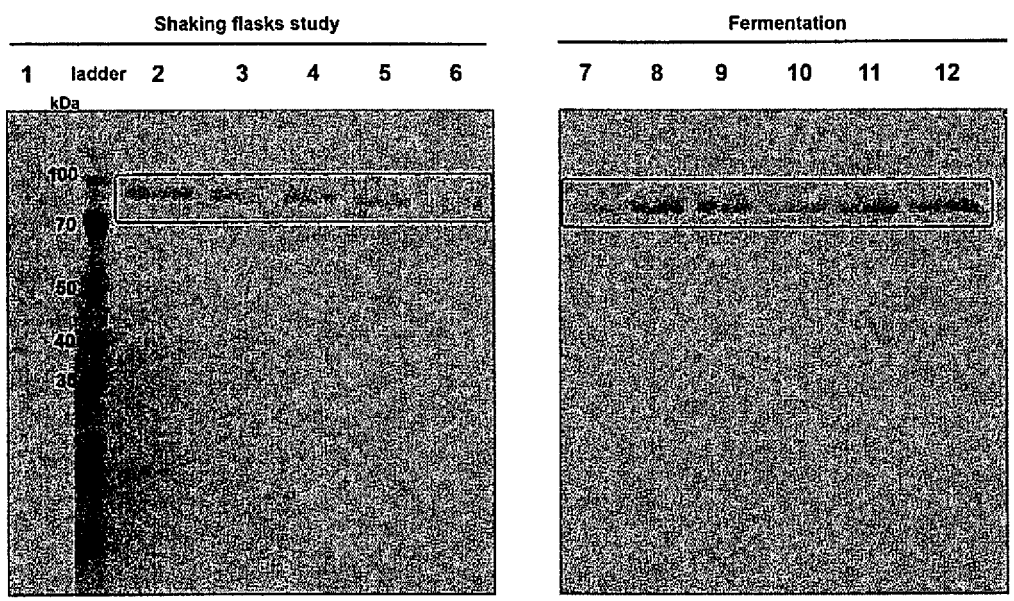
Figure 6:
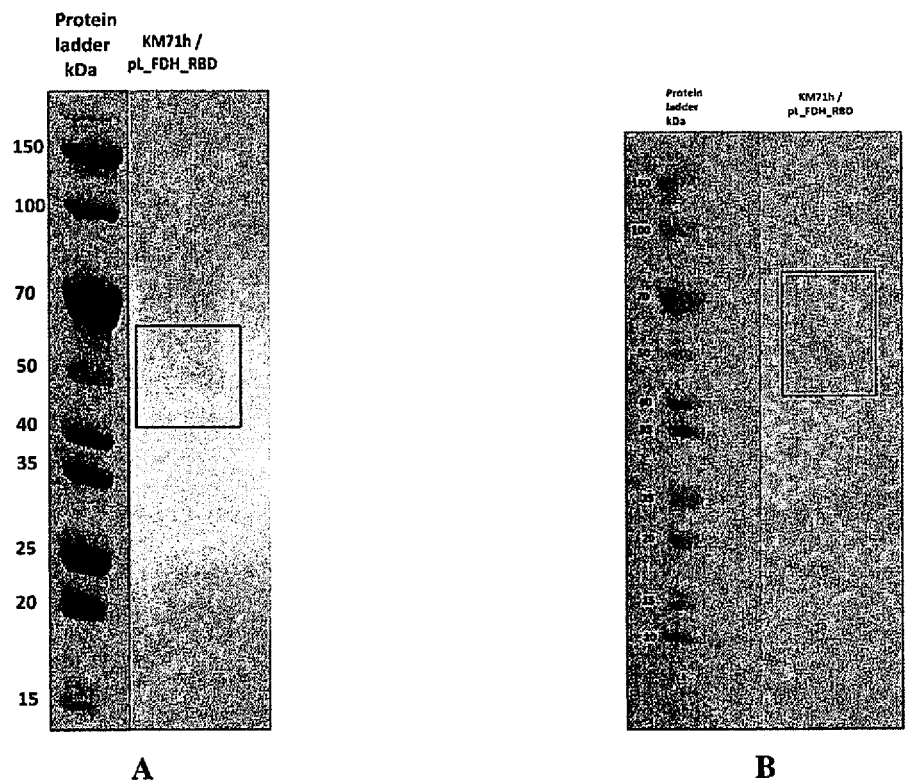

Cloning hEGF, hSOD3 and hLF to pL Integration Vector, Transformation into Yeast Strain and Screening The codon optimized genes of hEGF (SEQ ID NO:14), hSOD3 (SEQ ID NO:15), hLF (SEQ ID 16) and RBD (SEQ ID NO:21) were cloned to the standard plasmid pL_FDH with the NheI and PacI cloning sites, yielding the plasmids pL_hEGF, pL_hSOD3, pL_hLF and pL_RBD respectively. GOI (gene(s) of interest)—hEGF or hSOD3 or hLF or RBD were fused at their 5' with αMF secretion tag and cloned downstream of the inducible FDH promoter. The plasmids were linearized with Bsp119I restriction site and transformed into GS115 strain of *Pichia pastoris* by electroporation, using BTX electroporation (BTX, USA) according to the manufacturer's protocol. FIG. 2 schematically illustrates the construct containing the GOI and its integration within the yeast genome. Resistance to G418 antibiotic was used for the selection of the transformed clones. Thus, after the transformation the yeast culture was plated onto YPD plates with G418 (0.8 mg/ml). The integration of the respective GOI was verified with PCR using forward primer annealing to 3' of pFDH and reverse primer annealing to 5' of the GOI.

At least 10 positive clones were grown in the shaking flasks. Selected clones of the recombinant strains GS115/pL_hEGF, GS115/pL_hSOD3, GS115/pL_hLF and GS115/pL_RBD were inoculated into 10 ml of BMGY medium, incubated in temperature controlled orbital shaker for 24 hours at 29° C., 270 RPM. Pre-grown culture was then spun down at 2000 g, washed in distilled water divided into two aliquots. Each aliquot was re-inoculated into 10 ml of BMFSY medium, incubated for another 72 hours at 29° C., 270 RPM in the shaking flasks under inducible conditions. After 24-hours the cultures were induced for 3 consecutive days with a daily dose of the final concentration of 0,2% (w/v) potassium formate+1% (w/v) sorbitol.

YPD liquid: 10 g of Yeast extract; 20 g of Peptone; 20 g Dextrose; bring to 1 L with distilled water.

YPD agar: 10 g of Yeast extract; 20 g of Peptone; 20 g Dextrose; 20 g Agar; bring to 1 L with distilled water.

BMGY: 10 g of Yeast extract; 20 g of Peptone; 100 ml of 1 mM of Potassium phosphate buffer; 6.7 g of Yeast Nitrogen Base with Ammonium sulphate; 10 g of Glycerol; bring to 1 L with distilled water.

BMSFY: 10 g of Yeast extract; 20 g of Peptone; 100 ml of 1 mM of Potassium phosphate buffer pH 6.0; 6,7 g of Yeast Nitrogen Base with Ammonium sulphate; 20 g of Sorbitol; 0,5 g of Potassium formate; bring to 1l with distilled water.

Example 3

Fermentation (Culturing) the Selected Clones of the Following Recombinant Strain GS115/pL_hEGF, GS115/pL_hSOD3, GS115/pL_hLF The recombinant strains of *Pichia pastoris* GS115/pL_hEGF, GS115/pL_hSOD3, GS115/pL_hLF were used to carry out the fermentation to produce hEGF, hSOD3 and hLF respectively. Fermentation was carried out in a temperature-controlled fermenter (10 L working volume) to maintain the temperature at 28° C. The pH of the medium throughout the fermentation was controlled automatically using a pH probe, a controller (New Brunswick, BioFlo 3000) and a computer with Biocommand batch software (Eppendorf AG) was used to monitor and control the fermentation.

Fermentation was carried out using a cell culture medium comprising reduced basal salts medium (BSM) with PTM1 trace salts and kanamycin (50 mg/L optionally). The ingredients (per 1 liter) of BSM are listed in Table 2.

The culturing or each strain was carried out at 25° C. and a dissolved oxygen (DO) content in the medium at a level of 20% or higher. The pH during fermentation was maintained at 6.5 for secreting protein into the medium and for optimal growth by titrating a solution of ammonium hydroxide into the fermentation vessel. The agitation rate was maintained in the range from about 500 rpm to about 1000 rpm to maintain the above-mentioned oxygen concentration in the medium. Aeration rate was carried out to provide about 0.1 to 1.0 volume of oxygen (in liters) per volume of fermentation culture (in liters) per minute (vvm), so as to maintain the above-mentioned dissolved oxygen concentration (DO) in the medium. A minimum amount of Antifoam A (cat. no. A5633) or Antifoam 204 (cat. no. A6426) (Sigma-Aldrich, St. Louis, Mo.) was used to avoid excess foaming which can cause denaturation of secreted protein and can contribute to reducing the headspace in the fermenter. For the carbon sources, glycerol and sorbitol were used at variable rates as the first carbon source and the second carbon source respectively. Here, glycerol was used as the first carbon source to accumulate cell mass and sorbitol was used as the second carbon source to sustain cell growth and for inducing protein expression.

TABLE 1

Reduced Basal Salts Medium (BSM)

| | |
|---|---|
| Phosphoric acid, 85% | 4.25 ml |
| Calcium sulfate | 0.136 g |
| Potassium sulfate | 2.86 g |
| Magnesium sulfate | 1.13 g |
| Potassium hydroxide | 0.64 g |
| Glycerol | 40 g |
| Water | bring the volume to 1 L |

Twelve (12) ml of filter-sterilized PTM1 trace salts was added to 1 L of BSM medium. The ingredients of PTM1 trace salts (per liter) are listed in Table 3.

TABLE 2

PTM1 trace salts (per 1 liter)

| | |
|---|---|
| Cupric sulfate-5H2O | 6.0 g |
| Sodium iodide | 0.08 g |
| Manganese sulfate-H2O | 3.0 g |
| Sodium molybdate-2H2O | 0.2 g |
| Boric Acid | 0.02 g |
| Cobalt chloride | 0.5 g |
| Zinc chloride | 20.0 g |
| Ferrous sulfate-7H2O | 65.0 g |
| Biotin | 0.2 g |
| Sulfuric Acid | 5.0 ml |
| Water to a final volume of 1 liter | |

Cell growth was monitored at various time points during fermentation by measuring the optical density (OD) of the culture at a wavelength of 600 nm ($OD_{600}$) and by measuring the wet cell weight. The metabolic rate of the culture was monitored by monitoring dissolved oxygen (DO) and changes in the concentration of dissolved oxygen in response to carbon availability.

Measurement of Dissolved Oxygen ("DO")

The second carbon source feeding rate was adjusted in response to DO levels.

The level of the carbon source in the culture is an important determinant for protein induction. For example, changes in the DO concentrations (DO spikes) can be used to determine whether all the glycerol is consumed from the culture before adding the second carbon source e.g., sorbitol. Monitoring the level of carbon source ensures that the sorbitol feed does not over accumulate in the fermenter.

Fermenter Preparation and Glycerol Batch Phase

Fermentation started with the preparation of a seed culture flask that was used as an inoculum. Typically, a flask containing a total of 5 mL of BMGY media was inoculated with 50 uL of glycerol stock of either GS115/pL_hEGF or GS115/pL_hSOD3 or GS115/pL_hLF. The inoculate was grown at 29° C., by shaking the flask at 250-300 rpm for 16-24 hours, until the optical density of the culture at 600 nm ($OD_{600}$) was 2-6. This initial culture was sub-cultured into a second flask containing 5 mL BMGY media for an additional 24 hrs. On day 3, the second flask was sub-cultured into a 2-liter flask containing 200 mL BMGY media for another 16-24 hours, or until the $OD_{600}$ of the culture was 2-6.

This 200 mL culture served as the inoculum for the fermenter. A fermenter containing 4 L of BSM was sterilized prior to inoculation with the yeast culture. After sterilization, the medium was cooled, and the temperature set to 28° C. DO and pH probes were calibrated according to the manufacturer protocol (Mettler Toledo<Germany). The medium was agitated with the Rushton impeller at 500RPM and higher and aerated at 1.0 vvm using compressed air to bring the DO of the medium to levels suitable for fermentation. The pH of the medium was adjusted to 6.5 using ammonium hydroxide prior to inoculation, followed by the aseptic addition of 4.35 ml of PTM1 trace salts per liter of fermentation medium. To avoid bacterial contamination, kanamycin was added to the medium at a final concentration of 100 ug/ml. This medium was inoculated using 200 mL of yeast culture of $OD_{600}$ at 5.0-6.0. The DO of the culture (medium+yeast cells) in the fermenter was measured following inoculation and was recorded as nearly 100%. After the fermentation started, DO was monitored and controlled by the controlling unit of the fermenter using PID (Proportional-Integrative-Derivative) algorithm. If the DO level of the culture dropped below 20%, agitation was increased to bring the DO level of the culture above 20%. pH was also monitored and controlled by the controlling unit of the fermenter using PID (Proportional-Integrative-Derivative) algorithm, and adjusted by titrating the culture with the 30% (v/v) solution of ammonium hydroxide by the controlling unit.

Complete consumption of added glycerol was indicated by a spike in DO levels to 100%. The length of time needed to consume all the glycerol can vary depending on the density of the initial inoculum.

Sampling of the culture to measure cell density and wet cell weight was performed at the end of the glycerol feed stage and later at least twice daily. Cell density was measured by withdrawing a 5 ml sample from the fermenter at each time point and using a 1 ml aliquot for measuring cell density at a wavelength of 600 nm. Additionally, cell growth was evaluated by measuring the wet cell weight, pH, microscopic purity, protein concentrations and activity.

The wet cell weight at this stage, after the glycerol fed-batch stage was in the range from about 90 g/liter to about 150 g/liter.

Glycerol Fed-Batch Phase

Once the glycerol provided in the fed-batch phase was consumed, cell biomass was further increased by initiating a steady feed of glycerol. The glycerol feed was initiated using a 50% w/v solution of glycerol containing 12 ml PTM1 trace salts per liter of glycerol. The feed rate was set to 18.15 ml/hr/liter of the initial fermentation volume. Glycerol feeding was carried out for about four hours or longer (see below), until the wet cell weight was about 300 g/liter. The level of expressed protein was found to depend in part on the wet cell weight of the cell pellet from the glycerol feeding stage of fermentation. The length of the glycerol feeding phase, therefore, was varied to optimize protein yield.

Transition Phase and Sorbitol Fed-Batch Phase

Once the wet cell weight of the culture during the glycerol feeding phase was about 250 g/liter to about 300 g/liter, the carbon source was switched from a first carbon source, glycerol, to a second carbon source, sorbitol. Such a transition from glycerol to sorbitol was carried out using a "mixed feed" of glycerol and sorbitol initially. During the mixed feed phase, glycerol feeding was slowly decreased from a rate of 18.15 ml/hr/L of culture medium to 0 ml/hr/L of culture medium over a period of 2 hours and the sorbitol feeding rate is slowly increased from 0 ml/hr/L of culture medium to 2.57 ml/hr/L of culture medium over the same 2 hours. The transition from a glycerol feed to a sorbitol feed was carried out at a rate that did not cause any significant spikes or drifts in the pH of the culture. Other surrogate measures of cell growth and cell health were also monitored during the transition phase.

Once the transition from a glycerol feed to a sorbitol feed was completed, induction of protein expression was initiated by introducing an aqueous solution of 50% sorbitol containing 12 ml PTM1 trace salts per liter of this sorbitol solution.

Increasing agitation up to 1000 RPM and pure oxygen was used to maintain the DO of the culture within a range of 20-25%. When the culture was fully adapted to sorbitol utilization (2-4 hours), the DO reading remained steady. After 2-4 hours at the 2.57 ml/hr/liter feed rate, the sorbitol feed rate was increased to about 5.13 ml/hr per liter initial fermentation volume. Then feed rate was adjusted once a day proportionally to the increase of biomass during the course of the fermentation.

Once the culture had adapted to sorbitol as the carbon source, the inducer (50% (w/v) solution of potassium formate) was added to the cell culture medium at the amount of 2 ml/L of culture medium every 12 hours.

The entire sorbitol fed-batch phase lasted approximately 72 hours with a total of approximately 0.75 L sorbitol fed per liter of initial volume. The cell density increased during the sorbitol fed-batch phase to a final level of 350 to 500 g/liter wet cells.

SDS-PAGE and Western Blot was used to visualize the hEGF or hSOD3 or hLF using harvested samples of the supernatant of the culture media at the end of fermentation.

Example 4

Analysis of the Samples with SDS-PAGE and Western Blot with Anti HA-Antibodies

The expression construct, which was integrated to the production strain genome, contained GOI fused with HA-tag at its C-terminus for detection and visualizing purposes and cloned downstream of the promoter FDH. Once either of hEGF, hSOD3, hLF or RBD was expressed and secreted into the media during fermentation, it could then be detected on Western blot with anti-HA-tag antibodies. The strain engineering including molecular cloning, transformation, PCR selection was done according to the standard protocols (Molecular Cloning: A Laboratory Manual, 3rd Edition, Cold Spring Harbor Laboratory Press, 2001).

The supernatant was harvested by centrifugation (10,000 g for 5 min) of the vials containing an aliquot of the culture. SDS-PAGE was done with the 10 ul of supernatant followed by the wet transfer to the PVDF membrane according to standard manufacturer's protocol (BioRad, USA). The membrane was then incubated with first anti HA-antibodies (cat. no sc-7392, Santa Cruz Biotechnology, USA) and then with anti-mouse goat antibodies (cat. No. G-21040, Invitrogen, USA) according to the standard protocol (Invitrogen, USA). The membrane was stained with the Pierce™ ECL Plus Western Blotting Substrate kit (cat. No. 32132, ThermoFisher Scientific, USA). The supernatant from a methanol-induced cultures was used as a reference signal (FIG. 3-6).

While the preferred embodiments of the invention have been described above, it will be recognized and understood that various modifications may be made therein, and the appended claims are intended to cover all such modifications which may fall within the spirit and scope of the invention.

TABLE 3

| Nucleotide SEQ ID No. | Corresponding Amino acids SEQ ID No. | Accessory Element |
|---|---|---|
| SEQ ID No. 1 | n/a | Promoter FDH ($NAD^+$-dependent formate dehydrogenase) |
| SEQ ID No. 2 | n/a | Promoter AOX2 (alcohol oxidase 2) |
| SEQ ID No. 3 | n/a | Promoter PEX14 (peroxin Pexl4p) |
| SEQ ID No. 4 | n/a | Promoter FGH (S-hydroxymethyl-glutathione hydrolase) |
| SEQ ID No. 5 | n/a | Promoter DAK (dihydroxyacetone kinase) |
| SEQ ID No. 6 | n/a | Promoter FBA2 (fructose 1,6-bisphosphate aldolase) |
| SEQ ID No. 7 | n/a | Promoter PEX5 (peroxisomal membrane signal receptor PTSI) |
| SEQ ID No. 8 | n/a | Promoter ADH2 (alcohol dehydrogenase 2) |
| SEQ ID No. 9 | n/a | Promoter CAT1 (catalase) |
| SEQ ID No. 10 | n/a | Promoter DAS1 (Dihydroxyacetone synthase 1) |
| SEQ ID No. 11 | n/a | Promoter DAS2 (Dihydroxyacetone synthase 2) |
| SEQ ID No. 12 | n/a | Promoter FLD1 (Formaldehyde dehydrogenase) |
| SEQ ID No. 13 | n/a | Plasmid pL |
| SEQ ID No. 14 | SEQ ID No. 17 | Gene/Protein hEGF, human epidermal growth factor |
| SEQ ID No. 15 | SEQ ID No. 18 | Gene/Protein hSOD3 extracellular superoxide dismutase [Cu—Zn] |
| SEQ ID No. 16 | SEQ ID No. 19 | Gene/Protein hLF human Lactoferrin |
| SEQ ID No. 20 | SEQ ID No. 21 | Gene/Protein RBD (Receptor Binding Domain of S (spike) protein of SARS-CoV-2 virus |

Nucleotide Sequences

SEQ ID NO: 1
ATTCTGGCCCTTGCACCTGATCGCGAAGGTGGAAATGGCAGAAGGATCAGCCTGGACGAAGCAACCAGTTCCAACTG

CTAAGTAAAGAAGATGCTAGACGAAGGAGACTTCAGAGGTGAAAAGTTTGCAAGAAGAGAGCTGCGGGAAATAAATT

TTCAATTTAAGGACTTGAGTGCGTCCATATTCGTGTACGTGTCCAACTGTTTTCCATTACCTAAGAAAAACATAAAG

ATTAAAAAGATAAACCCAATCGGGAAACTTTAGCGTGCCGTTTCGGATTCCGAAAAACTTTTGGAGCGCCAGATGAC

TATGGAAAGAGGAGTGTACCAAAATGGCAAGTCGGGGGCTACTCACCGGATAGCCAATACATTCTCTAGGAACCAGG

GATGAATCCAGGTTTTTGTTGTCACGGTAGGTCAAGCATTCACTTCTTAGGAATATCTCGTTGAAAGCTACTTGAAA

TCCCATTGGGTGCGGAACCAGCTTCTAATTAAATAGTTCGATGATGTTCTCTAAGTGGGACTCTACGGCTCAAACTT

CTACACAGCATCATCTTAGTAGTCCCTTCCCAAAACACCATTCTAGGTTTCGGAACGTAACGAAACAATGTTCCTCT

-continued

CTTCACATTGGGCCGTTACTCTAGCCTTCCGAAGAACCAATAAAAGGGACCGGCTGAAACGGGTGTGGAAACTCCTG

TCCAGTTTATGGCAAAGGCTACAGAAATCCCAATCTTGTCGGGATGTTGCTCCTCCCAAACGCCATATTGTACTGCA

GTTGGTGCGCATTTTAGGGAAAATTTACCCCAGATGTCCTGATTTTCGAGGGCTACCCCCAACTCCCTGTGCTTATA

CTTAGTCTAATTCTATTCAGTGTGCTGACCTACACGTAATGATGTCGTAACCCAGTTAAATGGCCGAAAAACTATTT

AAGTAAGTTTATTTCTCCTCCAGATGAGACTCTCCTTCTTTTCTCCGCTAGTTATCAAACTATAAACCTATTTTACC

TCAAATACCTCCAACATCACCCACTTAAACA

SEQ ID NO: 2
TTATTTTTTGACCGAATTCTTTTTTTCAGACCATATGACCGGTCCATCTTCTACGGGGGATTATCTATGCTTTGAC

CTCTATCTTGATTCTTTTATGATTCAAATCACTTTTACGTTATTTATTACTTACTGGTTATTTACTTAGCGCCTTTT

CTGAAAAACATTTACTAAAAATCATACATCGGCACTCTCAAACACGACAGATTGTGATCAAGAAGCAGAGACAATCA

CCACTAAGGTTGCACATTTGAGCCAGTAGGCTCCTAATAGAGGTTCGATACTTATTTTGATAATACGACATATTGTC

TTACCTCTGAATGTGTCAATACTCTCTCGTTCTTCGTCTCGTCAGCTAAAAATATAACACTTCGAGTAAGATACGCC

CAATTGAAGGCTACGAGATACCAGACTATCACTAGTAGAACTTTGACATCTGCTAAAGCAGATCAAATATCCATTTA

TCCAGAATCAATTACCTTCCTTTAGCTTGTCGAAGGCATGAAAAAGCTACATGAAAATCCCCATCCTTGAAGTTTTG

TCAGCTTAAAGGACTCCATTTCCTAAAATTTCAAGCAGTCCTCTCAACTAAATTTTTTCCATTCCTCTGCACCCAG

CCCTCTTCATCAACCGTCCAGCCTTCTCAAAAGTCCAATGTAAGTAGCCTGCAAATTCAGGTTACAACCCCTCAATT

TTCCATCCAAGGGCGATCCTTACAAAGTTAATATCGAACAGCAGAGACTAAGCGAGTCATCATCACCACCCAACGAT

GGTGAAAAACTTTAAGCATAGATTGATGGAGGGTGTATGGCACTTGGCGGCTGCATTAGAGTTTGAAACTATGGGGT

AATACATCACATCCGGAACTGATCCGACTCCGAGATCATATGCAAAGCACGTGATGTACCCCGTAAACTGCTCGGAT

TATCGTTGCAATTCATCGTCTTAAACAGTACAAGAAACTTTATTCATGGGTCATTGGACTCTGATGAGGGGCACATT

TCCCCAATGATTTTTTGGGAAAGAAAGCCGTAAGAGGACAGTTAAGCGAAAGAGACAAGACAACGAACAGCAAAAGT

GACAGCTGTCAGCTACCTAGTGGACAGTTGGGAGTTTCCAATTGGTTGGTTTTGAATTTTTACCCATGTTGAGTTGT

CCTTGCTTCTCCTTGCAAACAATGCAAGTTGATAAGACATCACCTTCCAAGATAGGCTATTTTTGTCGCATAAATTT

TTGTCTCGGAGTGAAAACCCCTTTTATGTGAACAGATTACAGAAGCGTCCTACCCTTCACCGGTTGAGATGGGGAGA

AAATTAAGCGATGAGGAGACGATTATTGGTATAAAAGAAGCAACCAAAATCCCTTATTGTCCTTTTCTGATCAGCAT

CAAAGAATATTGTCTTAAAACGGGCTTTTAACTACATTGTTCTTACACATTGCAAACCTCTTCCTTCTATTTCGGAT

CAACTGTATTGACTACATTGATCTTTTTTAACGAAGTTTACGACTTACTAAATCCCCACAAACAAATCAACTGAGAA

AA

SEQ ID NO: 3
ATTCTGGCCCTTGCACCTGATCGCGAAGGTGGAAATGGCAGAAGGATCAGCCTGGACGAAGCAACCAGTTCCAACTG

CTAAGTAAAGAAGATGCTAGACGAAGGAGACTTCAGAGGTGAAAAGTTTGCAAGAAGAGAGCTGCGGGAAATAAATT

TTCAATTTAAGGACTTGAGTGCGTCCATATTCGTGTACGTGTCCAACTGTTTTCCATTACCTAAGAAAAACATAAAG

ATTAAAAAGATAAACCCAATCGGGAAACTTTAGCGTGCCGTTTCGGATTCCGAAAAACTTTTGGAGCGCCAGATGAC

TATGGAAAGAGGAGTGTACCAAAATGGCAAGTCGGGGGCTACTCACCGGATAGCCAATACATTCTCTAGGAACCAGG

GATGAATCCAGGTTTTTGTTGTCACGGTAGGTCAAGCATTCACTTCTTAGGAATATCTCGTTGAAAGCTACTTGAAA

TCCCATTGGGTGCGGAACCAGCTTCTAATTAAATAGTTCGATGATGTTCTCTAAGTGGGACTCTACGGCTCAAACTT

CTACACAGCATCATCTTAGTAGTCCCTTCCCAAAACACCATTCTAGGTTTCGGAACGTAACGAAACAATGTTCCTCT

CTTCACATTGGGCCGTTACTCTAGCCTTCCGAAGAACCAATAAAAGGGACCGGCTGAAACGGGTGTGGAAACTCCTG

TCCAGTTTATGGCAAAGGCTACAGAAATCCCAATCTTGTCGGGATGTTGCTCCTCCCAAACGCCATATTGTACTGCA

GTTGGTGCGCATTTTAGGGAAAATTTACCCCAGATGTCCTGATTTTCGAGGGCTACCCCCAACTCCCTGTGCTTATA

CTTAGTCTAATTCTATTCAGTGTGCTGACCTACACGTAATGATGTCGTAACCCAGTTAAATGGCCGAAAAACTATTT

-continued

AAGTAAGTTTATTTCTCCTCCAGATGAGACTCTCCTTCTTTTCTCCGCTAGTTATCAAACTATAAACCTATTTTACC

TCAAATACCTCCAACATCACCCACTTAAACA

SEQ ID NO: 4
ATCTTCATTGATGAAACGTTGTGATCGGTGTGACTTTTATAGTAAAAGCTACAACTGTTTGAAATACCAAGATATCA

TTGTGAATGGCTCAAAAGGGTAATACATCTGAAAAACCTGAAGTGTGGAAAATTCCGATGGAGCCAACTCATGATAA

CGCAGAAGTCCCATTTTGCCATCTTCTCTTGGTATGAAACGGTAGAAAATGATCCGAGTATGCCAATTGATACTCTT

GATTCATGCCCTATAGTTTGCGTAGGGTTTAATTGATCTCCTGGTCTATCGATCTGGGACGCAATGTAGACCCCATT

AGTGGAAACACTGAAAGGGATCCAACACTCTAGGCGGACCCGCTCACAGTCATTTCAGGACAATCACCACAGGAATC

AACTACTTCTCCCAGTCTTCCTTGCGTGAAGCTTCAAGCCTACAACATAACACTTCTTACTTAATCTTTGATTCTCG

AATTGTTTACCCAATCTTGACAACTTAGCCTAAGCAATACTCTGGGGTTATATATAGCAATTGCTCTTCCTCGCTGT

AGCGTTCATTCCATCTTTCTA

SEQ ID NO: 5
TGTCATCTGCTGATGCTGTGAGGGAGAAAGAAGTAGGGGTGATACATGGTTTATAGGCAAAGCATGTTTGTTTCAGA

TCAAAGATTAGCGTTTCAAAGTTGTGGAAAAGTGACCATGCAACAATATGCAACACATTCGGATTATCTGATAAGTT

TCAAAGCTACTAAGTAAGCCCGTTTCAAGTCTCCAGACCGACATCTGCCATCCAGTGATTTTCTTAGTCCTGAAAAA

TACGATGTGTAAACATAAACCACAAAGATCGGCCTCCGAGGTTGAACCCTTACGAAAGAGACATCTGGTAGCGCCAA

TGCCAAAAAAAATCACACCAGAAGGACAATTCCCTTCCCCCCCAGCCCATTAAAGCTTACCATTTCCTATTCCAAT

ACGTTCCATAGAGGGCATCGCTCGGCTCATTTTCGCGTGGGTCATACTAGAGCGGCTAGCTAGTCGGCTGTTTGAGC

TCTCTAATCGAGGGGTAAGGATGTCTAATATGTCATAATGGCTCACTATATAAAGAACCCGCTTGCTCAACCTTCGA

CTCCTTTCCCGATCCTTTGCTTGTTGCTTCTTCTTTTATAACAGGAAACAAAGGAATTTATACACTTTAA

SEQ ID NO: 6
AAATTAATCCATAAGATAAGGCAAATGTGCTTAAGTAATTGAAAACAGTGTTGTGATTATATAAGCATGGTATTTGA

ATAGAACTACTGGGGTTAACTTATCTAGTAGGATGGAAGTTGAGGGAGATCAAGATGCTTAAAGAAAAGGATTGGCC

AATATGAAAGCCATAATTAGCAATACTTATTTAATCAGATAATTGTGGGCATTGTGACTTGACTTTTACCAGGACT

TCAAACCTCAACCATTTAAACAGTTATAGAAGACGTACCGTCACTTTTGCTTTTAATGTGATCTAAATGTGATCACA

TGAACTCAAACTAAAATGATATCTTTTACTGGACAAAAATGTTATCCTGCAAACAGAAAGCTTTCTTCTATTCTAAG

AAGAACATTTACATTGGTGGGAAACCTGAAAACAGAAAATAAATACTCCCCAGTGACCCTATGAGCAGGATTTTTGC

ATCCCTATTGTAGGCCTTTCAAACTCACACCTAATATTTCCCGCCACTCACACTATCAATGATCACTTCCCAGTTCT

CTTCTTCCCCTATTCGTACCATGCAACCCTTACACGCCTTTTCCATTTCGGTTCGGATGCGACTTCCAGTCTGTGGG

GTACGTAGCCTATTCTCTTAGCCGGTATTTAAACATACAAATTCACCCAAATTCTACCTTGATAAGGTAATTGATTA

ATTTCATAAAT

SEQ ID NO: 7
TCCAAACCAAACGGTCTAGCAAAAACGATAACTTTAAAGAACTTTTCAATTGGTTTTGTACACTACCACCGGTTTAC

TACCTCTGCCTTCGGTTCTTCTCCTCACATTTTTCGCAACTGGGATAGCGTAGCCTAAAGTGTCACATGCTCGCTGC

TCACATTCCCTACACAACAGAGATTGTCAGCAGAGGAAATTGAGCTCCACCATTCAACACTTGTGGATTATGATAG

TCTGTGCTATCAGCTCTCTTTTTTTTGTTGCTGTAGAATTTACCGTGCTAGCAACCTTTTAAACTTTGTTTAGCTCT

CCTTCCCTCTTCCATTCATCTGTTTCGGTCCGATCCGTCTCTGGTCATCTCCTCCGCATTTTTTTTTACCGTTAGC

GATAGGGGTCAGATCAATTCAATCAGTTTTGGCAAGGGTATTTAAAGGTGGCGAAATCCCCCTCCGTTTGTTGAACA

CATCCAACTATTCTCAACCCAACCATCTAACTAATCGTA

SEQ ID NO: 8
CGCAGCGTTTTCTGACGGTACTAGAGGACTCTTAGGGGAAGGTAGAATCAATAAAGATCATATTAGGTAAGCAAATT

TTGGATGGAATAGGAGACTAGGTGTGGATGCGCGATCTCGCCAAATTGCACGACCAGAGTGGATGCCGGATGGTGGT

AAACCGTTTCTTCCTTTTTACCACCCAAGTGCGAGTGAAACACCCCATGGCTGCTCTCCGATTGCCCCTCTACAGGC

```
ATAAGGGTGTGACTTTGTGGGCTTGAATTTTACACCCCCTCCAACTTTTCTCGCATCAATTGATCCTGTTACCAATA

TTGCATGCCCGGAGGAGACTTGCCCCCTAATTTCGCGGCGTCGTCCCGGATCGCAGGGTGAGACTGTAGAGACCCCA

CATAGTGACAATGATTATGTAAGAAGAGGGGGGTGATTCGGCCGGCTATCGAACTCTAACAACTAGGGGGTGAACA

ATGCCCAGCAGTCCTCCCCACTCTTTGACAAATCAGTATCACCGATTAACACCCCAAATCTTATTCTCAACGGTCCC

TCATCCTTGCACCCCTCTTTGGACAAATGGCAGTTAGCATTGGTGCACTGACTGACTGCCCAACCTTAAACCCAAAT

TTCTTAGAAGGGGCCCATCTAGTTAGCGAGGGGTGAAAAATTCCTCCATCGGAGATGTATTGACCGTAAGTTGCTGC

TTAAAAAAATCAGTTCAGATAGCGAGACTTTTTTGATTTCGCAACGGGAGTGCCTGTTCCATTCGATTGCAATTCT

CACCCCTTCTGCCCAGTCCTGCCAATTGCCCATGAATCTGCTAATTTCGTTGATTCCCACCCCCCTTTCCAACTCCA

CAAATTGTCCAATCTCGTTTTCCATTTGGGAGAATCTGCATGTCGACTACATAAAGCGACCGGTGTCCGAAAAGATC

TGTGTAGTTTTCAACATTTTGTGCTCCCCCCGCTGTTTGAAAACGGGGGTGAGCGCTCTCCGGGGTGCGAATTCGTG

CCCAATTCCTTTCACCCTGCCTATTGTAGACGTCAACCCGCATCTGGTGCGAATATAGCGCACCCCCAATGATCACA

CCAACAATTGGTCCACCCCTCCCCAATCTCTAATATTCACAATTCACCTCACTATAAATACCCCTGTCCTGCTCCCA

AATTCTTTTTCCTTCTTCCATCAGCTACTAGCTTTTATCTTATTTACTTTACGAAA
```

SEQ ID NO: 9
```
TGTGTCTGTAAATTTAAATCCAAAGAAAAATAAAGGGCACTACATAGAACAACACAATCAACCTACATAGCTCTCTT

TTTTTTTTTTTTTTTTTTTCTTTTTTGTTTTTTCTCAATTTTCTTCATTTTTTGCATTGTTACTACTCTCCCATT

AAGGGAAATTCTACCAGGAAAACCGAAGAAGACAAATGCAAAAGGGAAATATGAATACGCATGTATGCGCGCAAAAC

CGCACTTACAGAGGGCATTAGGACATT
```

SEQ ID NO: 10
```
AGCAATGATATAAACAACAATTGAGTGACAGGTCTACTTTGTTCTCAAAAGGCCATAACCATCTGTTTGCATCTCTT

ATCACCACACCATCCTCCTCATCTGGCCTTCAATTGTGGGGAACAACTAGCATCCCAACACCAGACTAACTCCACCC

AGATGAAACCAGTTGTCGCTTACCAGTCAATGAATGTTGAGCTAACGTTCCTTGAAACTCGAATGATCCCAGCCTTG

CTGCGTATCATCCCTCCGCTATTCCGCCGCTTGCTCCAACCATGTTTCCGCCTTTTTCGAACAAGTTCAAATACCTA

TCTTTGGCAGGACTTTTCCTCCTGCCTTTTTTAGCCTCAGGTCTCGGTTAGCCTCTAGGCAAATTCTGGTCTTCATA

CCTATATCAACTTTTCATCAGATAGCCTTTGGGTTCAAAAAAGAACTAAAGCAGGATGCCTGATATATAAATCCCAG

ATGATCTGCTTTTGAAACTATTTTCAGTATCTTGATTCGTTTACTTACAAACAACTATTGTTGATTTTATCTGGAGA

ATAATCGAACAAA
```

SEQ ID NO: 11
```
CATAATGATATTTGAGGGTGTTAGTTACTTCGTCTCCAGAGTAGCTTATAGGGAGAAAAACCGAGACAACGATGGAA

CTCCCATGTAGATTCCACCGCCCCAATTACTGTTTTGGGCAATCCTGTTGATAAGACGCATTCTAGAGTTGTTTCAT

GAAAGGGTTACGGGTGTTGATTGGTTTGAGATATGCCAGAGGACAGATCAATCTGTGGTTTGCTAAACTGGAAGTCT

GGTAAGGACTCTAGCAAGTCCGTTACTCAAAAAGTCATACCAAGTAAGATTACGTAACACCTGGGCATGACTTTCTA

AGTTAGCAAGTCACCAAGAGGGTCCTATTTAACGTTTGGCGGTATCTGAAACACAAGACTTGCCTATCCCATAGTAC

ATCATATTACCTGTCAAGCTATGCTACCCCACAGAAATACCCCAAAAGTTGAAGTGAAAAAATGAAAATTACTGGTA

ACTTCACCCCATAACAAACTTAATAATTTCTGTAGCCAATGAAAGTAAACCCCATTCAATGTTCCGAGATTTAGTAT

ACTTGCCCCTATAAGAAACGAAGGATTTCAGCTTCCTTACCCCATGAACAGAAATCTTCCATTTACCCCCCACTGGA

GAGATCCGCCCAAACGAACAGATAATAGAAAAAAGAAATTCGGACAAATAGAACACTTTCTCAGCCAATTAAAGTCA

TTCCATGCACTCCCTTTAGCTGCCGTTCCATCCCTTTGTTGAGCAACACCATCGTTAGCCAGTACGAAAGAGGAAAC

TTAACCGATACCTTGGAGAAATCTAAGGCGCGAATGAGTTTAGCCTAGATATCCTTAGTGAAGGGTTGTTCCGATAC

TTCTCCACATTCAGTCATAGATGGGCAGCTTTGTTATCATGAAGAGACGGAAACGGGCATTAAGGGTTAACCGCCAA
```

ATTATATAAAGACAACATGTCCCCAGTTTAAAGTTTTTCTTTCCTATTCTTGTATCCTGAGTGACCGTTGTGTTTAA

TATAACAAGTTCGTTTTAACTTAAGACCAAAACCAGTTACAACAAATTATAACCCCTCTAAACACTAAAGTTCACTC

TTATCAAACTATCAAACATCAAAA

SEQ ID NO: 12

TGAGATAACAGAGTTGGGTAACTAGAGAGAATAATAGACGTATGCATGATTACTACACAACGGATGTCGCACTCTTT

CCTTAGTTAAAACTATCATCCAATCACAAGATGCGGGCTGGAAAGACTTGCTCCCGAAGGATAATCTTCTGCTTCTA

TCTCCCTTCCTCATATGGTTTCGCAGGGCTCATGCCCCTTCTTCCTTCGAACTGCCCGATGAGGAAGTCCTTAGCCT

ATCAAAGAATTCGGGACCATCATCGATTTTTAGAGCCTTACCTGATCGCAATCAGGATTTCACTACTCATATAAATA

CATCGCTCAAAGCTCCAACTTTGCTTGTTCATACAATTCTTGATATTCAC

SEQ ID NO: 13

ATTCTGGCCCTTGCACCTGATCGCGAAGGTGGAAATGGCAGAAGGATCAGCCTGGACGAAGCAACCAGTTCCAACTG

CTAAGTAAAGAAGATGCTAGACGAAGGAGACTTCAGAGGTGAAAAGTTTGCAAGAAGAGAGCTGCGGGAAATAAATT

TTCAATTTAAGGACTTGAGTGCGTCCATATTCGTGTACGTGTCCAACTGTTTTCCATTACCTAAGAAAAACATAAAG

ATTAAAAAGATAAACCCAATCGGGAAACTTTAGCGTGCCGTTTCGGATTCCGAAAAACTTTTGGAGCGCCAGATGAC

TATGGAAAGAGGAGTGTACCAAAATGGCAAGTCGGGGGCTACTCACCGGATAGCCAATACATTCTCTAGGAACCAGG

GATGAATCCAGGTTTTTGTTGTCACGGTAGGTCAAGCATTCACTTCTTAGGAATATCTCGTTGAAAGCTACTTGAAA

TCCCATTGGGTGCGGAACCAGCTTCTAATTAAATAGTTCGATGATGTTCTCTAAGTGGGACTCTACGGCTCAAACTT

CTACACAGCATCATCTTAGTAGTCCCTTCCCAAAACACCATTCTAGGTTTCGGAACGTAACGAAACAATGTTCCTCT

CTTCACATTGGGCCGTTACTCTAGCCTTCCGAAGAACCAATAAAAGGGACCGGCTGAAACGGGTGTGGAAACTCCTG

TCCAGTTTATGGCAAAGGCTACAGAAATCCCAATCTTGTCGGGATGTTGCTCCTCCCAAACGCCATATTGTACTGCA

GTTGGTGCGCATTTTAGGGAAAATTTACCCCAGATGTCCTGATTTTCGAGGGCTACCCCCAACTCCCTGTGCTTATA

CTTAGTCTAATTCTATTCAGTGTGCTGACCTACACGTAATGATGTCGTAACCCAGTTAAATGGCCGAAAAACTATTT

AAGTAAGTTTATTTCTCCTCCAGATGAGACTCTCCTTCTTTTCTCCGCTAGTTATCAAACTATAAACCTATTTTACC

TCAAATACCTCCAACATCACCCACTTAAACACGGCCGAATTCATAATGAGATTTCCTTCAATTTTTACTGCAGTTTT

ATTCGCAGCATCCTCCGCATTAGCTGCTCCAGTCAACACTACAACAGAAGATGAAACGGCACAAATTCCGGCTGAAG

CTGTCATCGGTTACTCAGATTTAGAAGGGGATTTCGATGTTGCTGTTTTGCCATTTTCCAACAGCACAAATAACGGG

TTATTGTTTATAAATACTACTATTGCCAGCATTGCTGCTAAAGAAGAAGGGGTATCTCTCGAGAAAAGAGAGGCTGA

AGCTTTAATTAACTGGGCCGCGAATTAATTCGCCTTAGACATGACTGTTCCTCAGTTCAAGTTGGGCACTTACGAGA

AGACCGGTCTTGCTAGATTCTAATCAAGAGGATGTCAGAATGCCATTTGCCTGAGAGATGCAGGCTTCATTTTTGAT

ACTTTTTTATTTGTAACCTATATAGTATAGGATTTTTTTTGTCATTTTGTTTCTTCTCGTACGAGCTTGCTCCTGAT

CAGCCTATCTCGCAGCTGATGAATATCTTGTGGTAGGGGTTTGGGAAAATCATTCGAGTTTGATGTTTTCTTGGTA

TTTCCCACTCCTCTTCAGAGTACAGAAGATTAAGTGAGACGTTCGTTTGTGCAAGCTTATCGATAAGCTTTAATGCG

GTAGTTTATCACAGTTAAATTGCTAACGCAGTCAGGCACCGTGTATGAAATCTAACAATGCGCTCATCGTCATCCTC

GGCACCGTCACCCTGGATGCTGTAGGCATAGGCTTGGTTATGCCGGTACTGCCGGGCCTCTTGCGGGATATCGTCCA

TTCCGACAGCATCGCCAGTCACTATGGCGTGCTGCTAGGTACAACTTGAGCAAGTTGTCGATCAGCTCCTCAAATTG

GTCCTCTGTAACGGATGACTCAACTTGCACATTAACTTGAAGCTCAGTCGATTGAGTGAACTTGATCAGGTTGTGCA

GCTGGTCAGCAGCATAGGGAAACACGGCTTTTCCTACCAAACTCAAGGAATTATCAAACTCTGCAACACTTGCGTAT

GCAGGTAGCAAGGGAAATGTCATACTTGAAGTCGGACAGTGAGTGTAGTCTTGAGAAATTCTGAAGCCGTATTTTTA

TTATCAGTGAGTCAGTCATCAGGAGATCCTCTACGCCGGACGCATCGTGGCCGACCTGCAGGGGGGGGGGGCGCT

GAGGTCTGCCTCGTGAAGAAGGTGTTGCTGACTCATACCAGCTGAATCGCCCCATCATCCAGCCAGAAAGTGAGGGA

GCCACGGTTGATGAGAGCTTTGTTGTAGGTGGACCAGTTGGTGATTTTGAACTTTTGCTTTGCCACGGAACGGTCTG

CGTTGTCGGGAAGATGCGTGATCTGATCCTTCAACTCAGCAAAAGTTCGATTTATTCAACAAAGCCGCCGTCCCGTC

-continued

AAGTCAGCGTAATGCTCTGCCAGTGTTACAACCAATTAACCAATTCTGATTAGAAAAACTCATCGAGCATCAAATGA
AACTGCAATTTATTCATATCAGGATTATCAATACCATATTTTTGAAAAAGCCGTTTCTGTAATGAAGGAGAAAACTC
ACCGAGGCAGTTCCATAGGATGGCAAGATCCTGGTATCGGTCTGCGATTCCGACTCGTCCAACATCAATACAACCTA
TTAATTTCCCCTCGTCAAAAATAAGGTTATCAAGTGAGAAATCACCATGAGTGACGACTGAATCCGGTGAGAATGGC
AAAAGCTTATGCATTTCTTTCCAGACTTGTTCAACAGGCCAGCCATTACGCTCGTCATCAAAATCACTCGCATCAAC
CAAACCGTTATTCATTCGTGATTGCGCCTGAGCGAGACGAAATACGCGATCGCTGTTAAAAGGACAATTACAAACAG
GAATCGAATGCAACCGGCGCAGGAACACTGCCAGCGCATCAACAATATTTTCACCTGAATCAGGATATTCTTCTAAT
ACCTGGAATGCTGTTTTCCCGGGGATCGCAGTGGTGAGTAACCATGCATCATCAGGAGTACGGATAAAATGCTTGAT
GGTCGGAAGAGGCATAAATTCCGTCAGCCAGTTTAGTCTGACCATCTCATCTGTAACATCATTGGCAACGCTACCTT
TGCCATGTTTCAGAAACAACTCTGGCGCATCGGGCTTCCCATACAATCGATAGATTGTCGCACCTGATTGCCCGACA
TTATCGCGAGCCCATTTATACCCATATAAATCAGCATCCATGTTGGAATTTAATCGCGGCCTCGAGCAAGACGTTTC
CCGTTGAATATGGCTCATAACACCCCTTGTATTACTGTTTATGTAAGCAGACAGTTTTATTGTTCATGATGATATAT
TTTTATCTTGTGCAATGTAACATCAGAGATTTTGAGACACAACGTGGCTTTCCCCCCCCCCCCTGCAGGTCGGCATC
ACCGGCGCCACAGGTGCGGTTGCTGGCGCCTATATCGCCGACATCACCGATGGGGAAGATCGGGCTCGCCACTTCGG
GCTCATGAGCGCTTGTTTCGGCGTGGGTATGGTGGCAGGCCCCGTGGCCGGGGGACTGTTGGGCGCCATCTCCTTGC
ATGCACCATTCCTTGCGGCGGCGGTGCTCAACGGCCTCAACCTACTACTGGGCTGCTTCCTAATGCAGGAGTCGCAT
AAGGGAGAGCGTCGAGTATCTATGATTGGAAGTATGGGAATGGTGATACCCGCATTCTTCAGTGTCTTGAGGTCTCC
TATCAGATTATGCCCAACTAAAGCAACCGGAGGAGGAGATTTCATGGTAAATTTCTCTGACTTTTGGTCATCAGTAG
ACTCGAACTGTGAGACTATCTCGGTTATGACAGCAGAAATGTCCTTCTTGGAGACAGTAAATGAAGTCCCACCAATA
AAGAAATCCTTGTTATCAGGAACAAACTTCTTGTTTCGAACTTTTTCGGTGCCTTGAACTATAAAATGTAGAGTGGA
TATGTCGGGTAGGAATGGAGCGGGCAAATGCTTACCTTCTGGACCTTCAAGAGGTATGTAGGGTTTGTAGATACTGA
TGCCAACTTCAGTGACAACGTTGCTATTTCGTTCAAACCATTCCGAATCCAGAGAAATCAAAGTTGTTTGTCTACTA
TTGATCCAAGCCAGTGCGGTCTTGAAACTGACAATAGTGTGCTCGTGTTTTGAGGTCATCTTTGTATGAATAAATCT
AGTCTTTGATCTAAATAATCTTGACGAGCCAAGGCGATAAATACCCAAATCTAAAACTCTTTTAAAACGTTAAAAGG
ACAAGTATGTCTGCCTGTATTAAACCCCAAATCAGCTCGTAGTCTGATCCTCATCAACTTGAGGGGCACTATCTTGT
TTTAGAGAAATTTGCGGAGATGCGATATCGAGAAAAAGGTACGCTGATTTTAAACGTGAAATTTATCTCAAGATCTC
TGCCTCGCGCGTTTCGGTGATGACGGTGAAAACCTCTGACACATGCAGCTCCCGGAGACGGTCACAGCTTGTCTGTA
AGCGGATGCCGGGAGCAGACAAGCCCGTCAGGGCGCGTCAGCGGGTGTTGGCGGGTGTCGGGGCGCAGCCATGACCC
AGTCACGTAGCGATAGCGGAGTGTATACTGGCTTAACTATGCGGCATCAGAGCAGATTGTACTGAGAGTGCACCATA
TGCGGTGTGAAATACCGCACAGATGCGTAAGGAGAAAATACCGCATCAGGCGCTCTTCCGCTTCCTCGCTCACTGAC
TCGCTGCGCTCGGTCGTTCGGCTGCGGCGAGCGGTATCAGCTCACTCAAAGGCGGTAATACGGTTATCCACAGAATC
AGGGGATAACGCAGGAAAGAACATGTGAGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCAATGCTCACGCTGTAGGTATCTCAGTTCGGTGT
AGGTCGTTCGCTCCAAGCTGGGCTGTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCAAACAAACCACCGCTGGTAGC
GGTGGTTTTTTTGTTTGCAAGCAGCAGATTACGCGCAGAAAAAAAGGATCTCAAGAAGATCCTTTGATCTTTTCTAC

-continued

GGGGTCTGACGCTCAGTGGAACGAAAACTCACGTTAAGGGATTTTGGTCATGAGATTATCAAAAAGGATCTTCACCT

AGATCCTTTTAAATTAAAAATGAAGTTTTAAATCAATCTAAAGTATATATGAGTAAACTTGGTCTGACAGTTACCAA

TGCTTAATCAGTGAGGCACCTATCTCAGCGATCTGTCTATTTCGTTCATCCATAGTTGCCTGACTCCCCGTCGTGTA

GATAACTACGATACGGGAGGGCTTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTCCTGCAACTTTATCCGCCTCCATC

CAGTCTATTAATTGTTGCCGGGAAGCTAGAGTAAGTAGTTCGCCAGTTAATAGTTTGCGCAACGTTGTTGCCATTGC

TGCAGGCATCGTGGTGTCACGCTCGTCGTTTGGTATGGCTTCATTCAGCTCCGGTTCCCAACGATCAAGGCGAGTTA

CATGATCCCCCATGTTGTGCAAAAAAGCGGTTAGCTCCTTCGGTCCTCCGATCGTTGTCAGAAGTAAGTTGGCCGCA

GTGTTATCACTCATGGTTATGGCAGCACTGCATAATTCTCTTACTGTCATGCCATCCGTAAGATGCTTTTCTGTGAC

TGGTGAGTACTCAACCAAGTCATTCTGAGAATAGTGTATGCGGCGACCGAGTTGCTCTTGCCCGGCGTCAACACGGG

ATAATACCGCGCCACATAGCAGAACTTTAAAAGTGCTCATCATTGGAAAACGTTCTTCGGGGCGAAAACTCTCAAGG

ATCTTACCGCTGTTGAGATCCAGTTCGATGTAACCCACTCGTGCACCCAACTGATCTTCAGCATCTTTTACTTTCAC

CAGCGTTTCTGGGTGAGCAAAAACAGGAAGGCAAAATGCCGCAAAAAAGGGAATAAGGGCGACACGGAAATGTTGAA

TACTCATACTCTTCCTTTTTCAATATTATTGAAGCATTTATCAGGGTTATTGTCTCATGAGCGGATACATATTTGAA

TGTATTTAGAAAAATAAACAAATAGGGGTTCCGCGCACATTTCCCCGAAAAGTGCCACCTGACGTC

SEQ ID NO: 14
AATAGTGACTCTGAATGCCCTTTGTCCCATGACGGATACTGTCTTCACGACGGCGTTTGTATGTATATCGAGGCACT

AGATAAGTATGCATGTAACTGCGTAGTAGGATACATTGGAGAACGTTGCCAATACCGTGATTTGAAGTGGTGGGAGT

TGCGT

SEQ ID NO: 15
TGGACGGGCGAGGACTCGGCGGAGCCCAACTCTGACTCGGCGGAGTGGATCCGAGACATGTACGCCAAGGTCACGGA

GATCTGGCAGGAGGTCATGCAGCGGCGGGACGACGACGGCGCGCTCCACGCCGCCTGCCAGGTGCAGCCGTCGGCCA

CGCTGGACGCCGCGCAGCCCCGGGTGACCGGCGTCGTCCTCTTCCGGCAGCTTGCGCCCCGCGCCAAGCTCGACGCC

TTCTTCGCCCTGGAGGGCTTCCCCGACCGAGCCGAACAGCTCCAGCCGCGCCATCCACGTGCACCAGTTCGGGGACCT

GAGCCAGGGCTGCGAGTCCACCGGGCCCCACTACAACCCGCTGGCCGTGCCGCACCCGCAGCACCCGGGCGACTTCG

GCAACTTCGCGGTCCGCGACGGCAGCCTCTGGAGGTACCGCGCCGGCCTGGCCGCCTCGCTCGCGGGCCCGCACTCC

ATCGTGGGCCGGGCCGTGGTCGTCCACGCTGGCGAGGACGACCTGGGCCGCGGCGGTAACCAGGCCAGCGTGGAGAA

CGGGAACGCGGGCCGGCGGCTGGCCTGCTGCGTGGTGGGCGTGTGCGGGCCCGGGCTCTGGGAGCGCCAGGCGCGGG

AGCACTCAGAGCGCAAGAAGCGGCGGCGCGAGAGCGAGTGCAAGGCCGCC

SEQ ID NO: 16
GGCCGTAGGAGAAGGAGTGTTCAGTGGTGCGCCGTATCCCAACCCGAGGCCACAAAATGCTTCCAATGGCAAAGGAA

TATGAGAAAAGTGCGTGGCCCTCCTGTCAGCTGCATAAAGAGAGACTCCCCCATCCAGTGTATCCAGGCCATTGCGG

AAAACAGGGCCGATGCTGTGACCCTTGATGGTGGTTTCATATACGAGGCAGGCCTGGCCCCCTACAAACTGCGACCT

GTAGCGGCGGAAGTCTACGGGACCGAAAGACAGCCACGAACTCACTATTATGCCGTGGCTGTGGTGAAGAAGGGCGG

CAGCTTTCAGCTGAACGAACTGCAAGGTCTGAAGTCCTGCCACACAGGCCTTCGCAGGACCGCTGGATGGAATGTCC

CTATAGGGACACTTCGTCCATTCTTGAATTGGACGGGTCCACCTGAGCCCATTGAGGCAGCTGTGGCCAGGTTCTTC

TCAGCCAGCTGTGTTCCCGGTGCAGATAAAGGACAGTTCCCCAACCTGTGTCGCCTGTGTGCGGGACAGGGGAAAA

CAAATGTGCCTTCTCCTCCCAGGAACCGTACTTCAGCTACTCTGGTGCCTTCAAGTGTCTGAGAGACGGGGCTGGAG

ACGTGGCTTTTATCAGAGAGAGCACAGTGTTTGAGGACCTGTCAGACGAGGCTGAAAGGGACGAGTATGAGTTACTC

TGCCCAGACAACACTCGGAAGCCAGTGGACAAGTTCAAAGACTGCCATCTGGCCCGGGTCCCTTCTCATGCCGTTGT

GGCACGAAGTGTGAATGGCAAGGAGGATGCCATCTGGAATCTTCTCCGCCAGGCACAGGAAAAGTTTGGAAAGGACA

AGTCACCGAAATTCCAGCTCTTTGGCTCCCCTAGTGGGCAGAAAGATCTGCTGTTCAAGGACTCTGCCATTGGGTTT

-continued

```
TCGAGGGTGCCCCCGAGGATAGATTCTGGGCTGTACCTTGGCTCCGGCTACTTCACTGCCATCCAGAACTTGAGGAA

AAGTGAGGAGGAAGTGGCTGCCCGGCGTGCGCGGGTCGTGTGGTGTGCGGTGGGCGAGCAGGAGCTGCGCAAGTGTA

ACCAGTGGAGTGGCTTGAGCGAAGGCAGCGTGACCTGCTCCTCGGCCTCCACCACAGAGGACTGCATCGCCCTGGTG

CTGAAAGGAGAAGCTGATGCCATGAGTTTGGATGGAGGATATGTGTACACTGCAGGCAAATGTGGTTTGGTGCCTGT

CCTGGCAGAGAACTACAAATCCCAACAAAGCAGTGACCCTGATCCTAACTGTGTGGATAGACCTGTGGAAGGATATC

TTGCTGTGGCGGTGGTTAGGAGATCAGACACTAGCCTTACCTGGAACTCTGTGAAAGGCAAGAAGTCCTGCCACACC

GCCGTGGACAGGACTGCAGGCTGGAATATCCCCATGGGCCTGCTCTTCAACCAGACGGGCTCCTGCAAATTTGATGA

ATATTTCAGTCAAAGCTGTGCCCCTGGGTCTGACCCGAGATCTAATCTCTGTGCTCTGTGTATTGGCGACGAGCAGG

GTGAGAATAAGTGCGTGCCCAACAGCAACGAGAGATACTACGGCTACACTGGGGCTTTCCGGTGCCTGGCTGAGAAT

GCTGGAGACGTTGCATTTGTGAAAGATGTCACTGTCTTGCAGAACACTGATGGAAATAACAATGAGGCATGGGCTAA

GGATTTGAAGCTGGCAGACTTTGCGCTGCTGTGCCTCGATGGCAAACGGAAGCCTGTGACTGAGGCTAGAAGCTGCC

ATCTTGCCATGGCCCCGAATCATGCCGTGGTGTCTCGGATGGATAAGGTGGAACGCCTGAAACAGGTGTTGCTCCAC

CAACAGGCTAAATTTGGGAGAAATGGATCTGACTGCCCGGACAAGTTTTGCTTATTCCAGTCTGAAACCAAAAACCT

TCTGTTCAATGACAACACTGAGTGTCTGGCCAGACTCCATGGCAAAACAACATATGAAAAATATTTGGGACCACAGT

ATGTCGCAGGCATTACTAATCTGAAAAAGTGCTCAACCTCCCCCCTCCTGGAAGCCTGTGAGTTCCTCAGGAAG
```

SEQ ID NO: 20
```
GTACAGCCTACAGAAAGTATTGTCCGTTTCCCTAATATCACCAATTTATGCCCTTTTGGTGAAGTCTTCAATGCCAC

CAGATTCGCCTCCGTATATGCCTGGAACCGTAAGAGAATCAGTAATTGCGTGGCCGATTATTCTGTGTTGTATAATA

GTGCCTCCTTCTCCACCTTCAAGTGTTATGGCGTGTCCCCTACTAAGCTGAATGACTTATGTTTTACCAATGTTTAT

GCAGACTCATTCGTCATCCGTGGAGATGAAGTCCGTCAAATTGCCCCCGGACAGACAGGAAAAATCGCCGACTATAA

TTATAAACTGCCTGATGACTTCACCGGATGTGTCATCGCATGGAATAGTAATAATTTAGATTCAAAAGTAGGAGGAA

ATTATAATTATCTTTACCGTCTGTTTAGAAAATCAAACTTGAAACCATTCGAGAGAGATATTTCCACAGAGATCTAC

CAGGCAGGATCCACCCCTTGCAATGGAGTCGAAGGATTCAATTGCTATTTTCCTCTGCAGTCTTATGGATTTCAGCC

TACAAATGGAGTCGGATACCAACCTTATAGAGTCGTGGTCTTAAGTTTCGAGTTGCTTCACGCCGTCGCCACAGTGT

GCGGACCTAAAAAGTCAACAAATTTAGTCAAGAAT
```

Amino Acid Sequences

SEQ ID NO: 17
NSDSECPLSHDGYCLHDGVCMYIEALDKYACNCVVGYIGERCQYRDLKWWELR

SEQ ID NO: 18
WTGEDSAEPNSDSAEWIRDMYAKVTEIWQEVMQRRDDDGALHAACQVQPSATLDAAQPRVTGVVLFRQLAPRAKLDA

FFALEGFPTEPNSSSRAIHVHQFGDLSQGCESTGPHYNPLAVPHPQHPGDFGNFAVRDGSLWRYRAGLAASLAGPHS

IVGRAVVVHAGEDDLGRGGNQASVENGNAGRRLACCVVGVCGPGLWERQAREHSERKKRRRESECKAA

SEQ ID NO: 19
GRRRRSVQWCAVSQPEATKCFQWQRNMRKVRGPPVSCIKRDSPIQCIQAIAENRADAVTLDGGFIYEAGLAPYKLRP

VAAEVYGTERQPRTHYYAVAVVKKGGSFQLNELQGLKSCHTGLRRTAGWNVPIGTLRPFLNWTGPPEPIEAAVARFF

SASCVPGADKGQFPNLCRLCAGTGENKCAFSSQEPYFSYSGAFKCLRDGAGDVAFIRESTVFEDLSDEAERDEYELL

CPDNTRKPVDKFKDCHLARVPSHAVVARSVNGKEDAIWNLLRQAQEKFGKDKSPKFQLFGSPSGQKDLLFKDSAIGF

SRVPPRIDSGLYLGSGYFTAIQNLRKSEEEVAARRARVVWCAVGEQELRKCNQWSGLSEGSVTCSSASTTEDCIALV

LKGEADAMSLDGGYVYTAGKCGLVPVLAENYKSQQSSDPDPNCVDRPVEGYLAVAVVRRSDTSLTWNSVKGKKSCHT

AVDRTAGWNIPMGLLFNQTGSCKFDEYFSQSCAPGSDPRSNLCALCIGDEQGENKCVPNSNERYYGYTGAFRCLAEN

AGDVAFVKDVTVLQNTDGNNNEAWAKDLKLADFALLCLDGKRKPVTEARSCHLAMAPNHAVVSRMDKVERLKQVLLH

QQAKFGRNGSDCPDKFCLFQSETKNLLFNDNTECLARLHGKTTYEKYLGPQYVAGITNLKKCSTSPLLEACEFLRK

-continued

SEQ ID NO: 21

VQPTESIVRFPNITNLCPFGEVFNATRFASVYAWNRKRISNCVADYSVLYNSASFSTFKCYGVSPTKLNDLCFTNVY

ADSFVIRGDEVRQIAPGQTGKIADYNYKLPDDFTGCVIAWNSNNLDSKVGGNYNYLRLFRKSNLKPFERDISTEIY

QAGSTPCNGVEGFNCYFPLQSYGFQPTNGVGYQPYRVVVLSFELLHAVATVCGPKKSTNLVKN

The invention claimed is:

1. A method for producing a transgenic cell product comprising:
(a) providing an expression system comprising: a methylotrophic yeast cell comprising an expression vector, said expression vector comprising an inducible MUT (Methanol Utilization) pathway promoter operably linked to a nucleic acid molecule encoding a recombinant protein of interest for producing a transgenic cell product of interest, wherein the inducible MUT pathway promoter is selected from the group consisting of: NAD+-dependent formate dehydrogenase (FDH) promoter: alcohol oxidase 2 (AOX2) promoter; peroxin Pex14p (PEX14) promoter; dihydroxyacetone kinase (DAK) promoter; dihydroxyacetone synthase 1,2 (DAS1,2) promoter; formyl-glutathione dehydrogenase (FGH) promoter: formaldehyde dehydrogenase 1 (FLD1) promoter: Fructose 1,6-bisphosphate aldolase (FBA) promoter: Peroxisomal membrane signal receptor PTS1 (PEX5) promoter; alcohol dehydrogenase 2 (ADH2) promoter; and catalase (CAT) promoter;

(b) growing the methylotrophic yeast cell on a suitable carbon source for supporting active growth of the methylotrophic yeast cell, thereby providing a methylotrophic yeast cell culture;

(c) after the methylotrophic yeast cell culture has attained a suitable methylotrophic yeast cell culture density, growing the methylotrophic yeast cell culture on a non-repressing carbon source selected from the group consisting of: sorbitol, mannitol, trehalose and alanine, thereby de-repressing the inducible MUT pathway promoter;
(d) adding an amount of an inducer compound selected from the group consisting of: S-formylglutathione; S-hydroxymethyl glutathione; formic acid; an alkali metal salt of formic acid; and an alkaline earth metal salt of formic acid; sufficient to induce the inducible MUT pathway promoter to the methylotrophic yeast cell culture such that the inducible MUT pathway promoter expresses the nucleic acid molecule encoding the recombinant protein of interest, thereby producing the transgenic cell product of interest; and
(e) recovering the transgenic cell product of interest from the methylotrophic yeast cell culture.

2. The method according to claim 1 wherein the methylotrophic yeast is selected from the group consisting of: *Pichia pastoris, Komagataella kurtzmanii, Komagataella phaffii, Pichia angusta, Pichia guillermordii, Pichia methanolica, Pichia inositovera, Hansenula polymorpha, Candida boidinii,* and *Yarrowia lipolytica.*

3. The method according to claim 1 wherein the methylotrophic yeast is *Pichia pastoris.*

4. The method according to claim 1 wherein the nucleic acid molecule further comprises a secretion peptide in frame with the recombinant protein of interest.

5. The method according to claim 1 wherein the nucleic acid molecule further comprises an expression tag in frame with the recombinant protein of interest.

6. The method according to claim 1 wherein the suitable methylotrophic yeast cell culture density is 250-350 g/L of culture (wet cell weight).

7. The method according to claim 1 wherein steps (c), (d) and (e) are repeated more than once.

8. The method according to claim 1 wherein the methylotrophic yeast cell culture density is determined so that the inducer compound is added at a concentration that is sufficient to induce the inducible promoter.

9. The method according to claim 1 wherein the non-repressing carbon source is initially added to the methylotrophic yeast cell culture in stages.

10. The method according to claim 1 wherein the suitable carbon source is glycerol or glucose.

11. A method for producing a transgenic cell product comprising:
(a) providing an expression system comprising: a methylotrophic yeast cell comprising an expression vector, said expression vector comprising an inducible MUT (Methanol Utilization) pathway promoter operably linked to a nucleic acid molecule encoding a recombinant protein of interest for producing a transgenic cell product of interest, wherein the inducible MUT pathway promoter is selected from the group consisting of: NAD+-dependent formate dehydrogenase (FDH) promoter; alcohol oxidase 2 (AOX2) promoter; peroxin Pex14p (PEX14) promoter; dihydroxyacetone kinase (DAK) promoter; dihydroxyacetone synthase 1,2 (DAS1,2) promoter; formyl-glutathione dehydrogenase (FGH) promoter: formaldehyde dehydrogenase 1 (FLD1) promoter: Fructose 1,6-bisphosphate aldolase (FBA) promoter; Peroxisomal membrane signal receptor PTS1 (PEX5) promoter; alcohol dehydrogenase 2 (ADH2) promoter; and catalase (CAT) promoter;
(b) growing the methylotrophic yeast cell on a suitable carbon source for supporting active growth of the methylotrophic yeast cell, thereby providing a methylotrophic yeast cell culture;
(c) after the methylotrophic yeast cell culture has attained a suitable methylotrophic yeast cell culture density:
(c1) adding to the methylotrophic yeast cell culture a non-repressing carbon source selected from the group consisting of sorbitol, mannitol, trehalose and alanine,
(c2) adding an amount of an inducer compound selected from the group consisting of: S-formylglutathione; S-hydroxymethyl glutathione; formic acid; an alkali metal or ammonium salt of formic acid; and an alkaline earth metal salt of formic acid; sufficient to induce the inducible MUT pathway promoter to the methylotrophic yeast cell culture such that the inducible MUT pathway promoter initiates expression of the nucleic acid molecule encoding the recombinant protein of interest, thereby producing the transgenic cell product of interest; and
(c3) recovering the transgenic cell product of interest from the methylotrophic yeast cell culture; and
(d) repeating steps (c1)-(c3).

12. The method according to claim 11 wherein the non-repressing carbon source is initially added to the methylotrophic yeast cell culture in stages, starting prior to exhaustion of the suitable carbon source so that initially the methylotrophic yeast cell culture is growing on both the suitable carbon source and the non-repressing carbon source.

13. The method according to claim 11 wherein the methylotrophic yeast is selected from the group consisting of: *Pichia pastoris, Komagataella kurtzmanii, Komagataella phaffii, Pichia angusta, Pichia guillermordil, Pichia methanolica, Pichia inositovera, Hansenula polymorpha, Candida boidinii,* and *Yarrowia lipolytica.*

14. The method according to claim 11 wherein the yeast is *Pichia pastoris.*

15. The method according to claim 11 wherein the nucleic acid molecule further comprises a secretion peptide in frame with the recombinant protein of interest.

16. The method according to claim 15 wherein the transgenic cell product of interest is recovered from the growth media and additional non-repressing carbon source and inducer compound are added to sustain growth of the methylotrophic yeast cell culture in batch phase so that the transgenic cell product of interested continues to be produced by the methylotrophic yeast cells and recovered from the media.

17. The method according to claim 11 wherein the nucleic acid molecule further comprises an expression tag in frame with the recombinant protein of interest.

18. The method according to claim 11 wherein the suitable methylotrophic yeast cell culture density is 250-350 g/L of culture (wet cell weight).

19. The method according to claim 11 wherein the methylotrophic yeast cell culture density is determined so that the inducer compound is added at a concentration that is sufficient to induce the inducible promoter.

20. The method according to claim 11 wherein the suitable carbon source is glycerol or glucose.

21. The method according to claim 1 wherein the inducer compound is selected from the group consisting of: S-formylglutathione; S-hydroxymethyl glutathione; an alkali metal salt of formic acid; and an alkaline earth metal salt of formic acid.

22. The method according to claim 11 wherein the inducer compound is selected from the group consisting of: S-formylglutathione; S-hydroxymethyl glutathione; an alkali metal salt of formic acid; and an alkaline earth metal salt of formic acid.

* * * * *